(12) United States Patent
Klintz et al.

(10) Patent No.: US 6,323,154 B1
(45) Date of Patent: Nov. 27, 2001

(54) 3-ARYLURACILS AND INTERMEDIATES FOR THEIR PREPARATION

(75) Inventors: Ralf Klintz, Grünstadt; Norbert Götz, Worms; Peter Schäfer, Ottersheim; Gerhard Hamprecht, Weinheim; Elisabeth Heistracher, Ludwigshafen; Christoph-Sweder von dem Bussche-Hünnefeld, Mannheim; Albrecht Harreus, Ludwigshafen; Karl-Otto Westphalen, Speyer; Helmut Walter, Obrigheim; Ulf Misslitz, Neustadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 08/894,749

(22) PCT Filed: Jan. 3, 1996

(86) PCT No.: PCT/EP96/00838

§ 371 Date: Aug. 26, 1997

§ 102(e) Date: Aug. 26, 1997

(87) PCT Pub. No.: WO96/28442

PCT Pub. Date: Sep. 19, 1996

(30) Foreign Application Priority Data

Mar. 15, 1995 (DE) ............................................. 195 08 590

(51) Int. Cl.$^7$ ..................... C07D 413/10; C07D 265/36; A01N 43/54; A01N 43/84
(52) U.S. Cl. ...................... 504/224; 504/225; 544/105
(58) Field of Search ....................... 504/225, 235, 504/239, 224; 544/105, 295

(56) References Cited

U.S. PATENT DOCUMENTS

| | | | |
|---|---|---|---|
| 4,981,508 | 1/1991 | Strunk et al. | 71/92 |
| 5,232,898 | 8/1993 | Suchy et al. | 544/243 |
| 5,310,723 | 5/1994 | Theodoridis | 504/243 |

FOREIGN PATENT DOCUMENTS

| | | |
|---|---|---|
| 230874 | 8/1987 | (EP). |
| 235567 | 9/1987 | (EP). |
| 408382 | 1/1991 | (EP). |
| 420194 | 4/1991 | (EP). |
| 477677 | 4/1992 | (EP). |
| 887559 | 10/1988 | (ZA). |

Primary Examiner—John M. Ford
(74) Attorney, Agent, or Firm—Keil & Weinkauf

(57) ABSTRACT

3-Aryluracils of the formula I

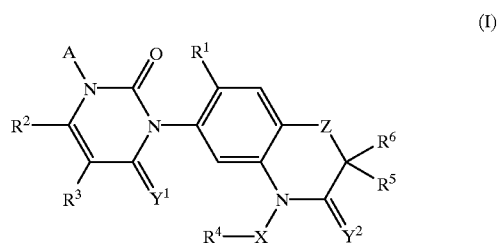

wherein
A is hydrogen, methyl or amino;
X is oxygen or —N($R^7$)— ($R^7$=H alkyl, alkenyl, alkynyl, alkylcarbonyl or alkoxyalkyl);
$Y^1$ is oxygen or sulfur;
Z is oxygen or —N($R^8$)— ($R^8$=H, alkyl, alkenyl, alkynyl or alkoxyalkyl);
$R^1$ is hydrogen or halogen;
$R^2$ is hydrogen, halogen, alkyl, haloalkyl, alkylthio, alkylsulfenyl or alkylsulfonyl;
$R^3$ is hydrogen, halogen or alkyl;
$R^4$ is hydrogen; or optionally substituted alkyl, cycloalkyl, haloalkyl, alkenyl, alkynyl, alkylcarbonyl, alkenylcarbonyl, alkynylcarbonyl or alkylsulfonyl,
$R^5$, $R^6$ are hydrogen, alkyl, alkenyl, alkynyl or alkoxyalkyl; or
$R^6$, $R^8$ are together a second chemical bond, methods and intermediates for their manufacture, and their use as herbicides or for the desiccation or defoliation of plants.

9 Claims, No Drawings

3-ARYLURACILS AND INTERMEDIATES FOR THEIR PREPARATION

This is a national phase application filed under 35 U.S.C. §371 of PCT/EP 96/00,838, filed Mar. 01, 1996.

The present invention relates to novel 3-aryluracils of the general formula I where the variables have the following meanings:

A is hydrogen, methyl oder amino;

$R^1$ is hydrogen or halogen;

$R^2$ is hydrogen, halogen, $C_1$–$C_6$-alkyl, $C_1$–$C_6$-haloalkyl, $C_1$–$C_6$-alkythio, $C_1$–$C_6$-alkylsulfenyl or $C_1$–$C_6$-alkylsulfonyl;

$R^3$ is hydrogen, halogen or $C_1$–$C_6$-alkyl;

X is oxygen or —N($R^7$)—, $R^7$ being hydrogen, $C_1$–$C_6$-alkyl, $C_3$–$C_6$-alkenyl, $C_3$–$C_6$-alkynyl, ($C_1$–$C_6$-alkyl)carbonyl or $C_1$–$C_6$-alkoxy-$C_1$–$C_6$-alkyl;

$Y^1$ and $Y^2$ independently of one another are oxygen or sulfur;

Z is oxygen or —N($R^8$)—;

$R^5$, $R^6$, $R^7$ and $R^8$ independently of one another are hydrogen, $C_1$–$C_6$-alkyl, $C_3$–$C_6$-alkenyl, $C_3$–$C_6$-alkynyl or $C_1$–$C_6$-alkoxy-$C_1$–$C_6$-alkyl;

or $R^6$ and $R^8$ together are a second chemical bond;

$R^4$ is hydrogen, $C_1$–$C_6$-alkyl, $C_3$–$C_8$-cycloalkyl, $C_1$–$C_6$-haloalkyl, $C_3$–$C_6$-alkenyl, $C_3$–$C_6$-alkynyl, ($C_1$–$C_6$-alkyl)carbonyl, ($C_3$–$C_6$-alkenyl)carbonyl, ($C_3$–$C_6$-alkynyl)carbonyl or $C_1$–$C_6$-alkylsulfonyl, it being possible for each of the last-mentioned 9 radicals to carry, if desired, one to three substituents, in each case selected from the group consisting of halogen, nitro, cyano, hydroxyl, $C_3$–$C_8$-cycloalkyl, $C_1$–$C_6$-alkoxy, $C_3$–$C_8$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfenyl, $C_1$–$C_6$-alkylsulfonyl, $C_1$–$C_6$-alkylideneaminooxy, the phenyl, phenoxy or phenylsulfonyl group, which can be unsubstituted or can carry one to three radicals, in each case selected from the group consisting of halogen, nitro, cyano, $C_1$–$C_6$-alkyl, $C_1$–$C_6$-alkoxy and $C_1$–$C_6$-haloalkyl, a 3- to 7-membered heterocyclyl, heterocyclyloxy, heterocyclylcarbonyl or heterocyclylcarbonyloxy group having one to three hetero atoms as ring members, selected from the group consisting of two oxygen atoms, two sulfur atoms and 3 nitrogen atoms, it being possible for the heterocycle to be saturated, partially or completely unsaturated or aromatic and, if desired, to carry one to three substituents, in each case selected from the group consisting of halogen, nitro, cyano, $C_1$–$C_6$-alkyl, $C_1$–$C_6$-alkoxy, $C_1$–$C_6$-haloalkyl and ($C_1$–$C_6$-alkyl)-carbonyl, a group —CO—$R^9$, —O—CO—$R^9$, —CO—$OR^9$, —O—CO—$OR^9$, —CO—$SR^9$, —O—CO—$SR^9$, —CO—N($R^9$)$R^{10}$, —O—CO—N($R^9$)$R^{10}$, —N($R^9$)$R^{10}$ or —C(NR")—$OR^{12}$, $R^9$ being hydrogen, $C_1$–$C_6$-alkyl, $C_3$–$C_8$-cycloalkyl, $C_3$–$C_6$-alkenyl, $C_3$–$C_6$-alkynyl, $C_1$–$C_6$-alkoxy-$C_1$–$C_6$-alkyl, ($C_1$–$C_6$-alkoxy)carbonyl-$C_1$–$C_6$-alkyl, phenyl or phenyl-$C_1$–$C_6$-alkyl, it being possible for the phenyl radicals to be unsubstituted or to carry one to three radicals, in each case selected from the group consisting of halogen, nitro, cyano, $C_1$–$C_6$-alkyl, $C_1$–$C_6$-alkoxy and $C_1$–$C_6$-haloalkyl $R^{10}$ being hydrogen, hydroxyl, $C_1$–$C_6$-alkyl, $C_3$–$C_8$-cycloalkyl or $C_1$–$C_6$-alkoxy, $C_3$–$C_6$ alkenyloxy or ($C_1$–$C_6$-alkoxy)carbonyl-$C_1$–$C_6$-alkoxy $R^{11}$ being $C_1$–$C_6$-alkoxy, $C_3$–$C_6$-alkenyloxy or ($C_1$–$C_6$-alkoxy)carbonyl-$C_1$–$C_6$-alkoxy and $R^{12}$ being $C_1$–$C_6$-alkyl, $C_3$–$C_6$-alkenyl or ($C_1$–$C_6$-alkoxy)-carbonyl-$C_1$–$C_1$–$C_6$-alkyl and the agriculturally utilizable salts of those compounds I in which A is hydrogen.

The invention additionally relates to the use of the compounds I as herbicides and/or for the desiccation and/or defoliation of plants, herbicidal compositions and compositions for the desiccation and/or defoliation of plants which comprise the compounds I as active substances, methods for controlling undesired vegetation and for the desiccation and/or defoliation of plants using the compounds I, processes for preparing the compounds I and herbicidal compositions and compositions for the desiccation and/or defoliation of plants using the compounds I, and novel intermediates of the formulae IV, V, VIII, X and XII, from which the compounds I are obtainable.

EP-A 420 194 already describes compounds of the formulae IIa and IIIa where $R^a$ is $C_1$–$C_7$-alkyl, $C_3$–$C_7$-alkenyl, $C_3$–$C_7$-alkynyl, halogen-$C_1$–$C_6$-alkyl, halogen-$C_3$–$C_6$-alkenyl or $C_1$–$C_4$-alkoxy-$C_1$–$C_3$-alkyl. The compounds IIa where A=methyl or amino and the compounds IIIa are ascribed herbicidal properties.

WO 90/15057 further discloses that, inter alia, compounds of the formula IIb

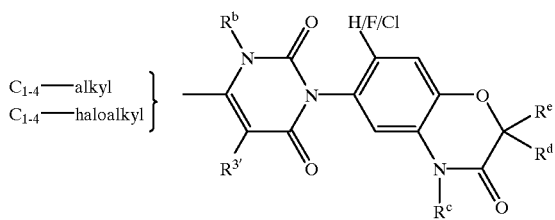

where
- $R^b$ is, inter alia, hydrogen or $C_1$–$C_4$-alkyl;
- $R^c$ is hydrogen or certain organic radicals bonded via carbon;
- $R^d$ and $R^e$ are in each case hydrogen, halogen, $C_1$–$C_4$-alkyl or phenyl and
- $R^{3'}$ is hydrogen, halogen or $C_1$–$C_4$-alkyl, are also herbicidally active.

3-(3-oxo-2H-1,4-benzoxazin-6-yl)-6-haloalkyl-2,4-(1H,3H)-pyrimidinedione derivatives of this type are further also disclosed in EP-A 408 382. They are described there as herbicides, together with compounds of the formulae IIIb and IIIc

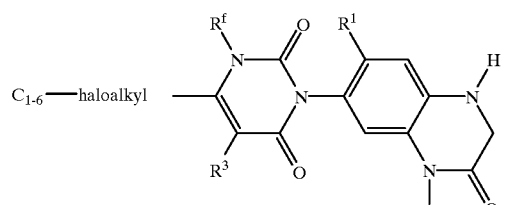

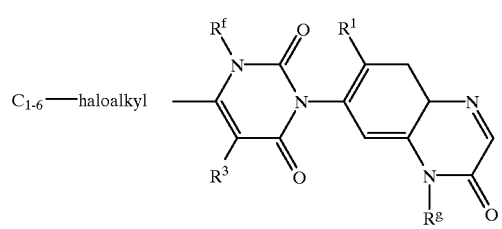

where
- $R^f$ is, inter alia, hydrogen or $C_1$–$C_3$-alkyl and
- $R^g$ is hydrogen or certain organic radicals bonded via carbon.

According to the disclosure of U.S. Pat. No. 5,310,723, 3-(1-lower alkoxy-quinolin-2-on-7-yl)-1-methyl-6-trifluoromethyluracils, inter alia, are also herbicidally active.

Finally, EP-A 477 677 relates to 6-(4,5,6,7-tetrahydro-2H-isoindole-1,3-dion-2-yl)-, 6-(dimethylmaleimido)- and 6-(4,5,6,7-tetrahydroisoindol-2-yl)-1,4-benzoxazin-3(4H)-one derivatives which on the nitrogen of the oxazine ring carry a $C_{1-5}$-alkoxy, $C_{3-4}$-alkenyloxy, $C_{3-4}$-alkynyloxy, cyclopropylmethoxy, $C_{2-3}$-cyanoalkoxy, $C_{1-2}$-alkoxy-$C_{1-2}$-alkoxy or $C_{1-2}$-alkylthio-$C_{1-2}$-alkoxy group. Herbicidal properties are also indicated for these compounds.

The herbicidal properties of the known compounds, however, are not always completely satisfactory.

It is an object of the present invention to provide novel active compounds, in particular herbicidally active compounds, using which undesired plants can be specifically controlled better than previously. The object also extends to the provision of novel compounds having desiccant/defoliant activity.

We have found that this object is achieved by the 3-aryluracils of the formula I and their herbicidal action.

Herbicidal compositions have further been found which comprise the compounds I and have a very good herbicidal action. Processes for preparing these compositions and methods of controlling undesired plant growth using the compounds I have additionally been found.

In addition, it has been found that the compounds I are also suitable for the defoliation and desiccation of parts of plants, for which suitable crop plants are those such as cotton, potato, rape, sunflower, soybean or field beans, in particular cotton. With respect to this, compositions for the desiccation and/or defoliation of plants, processes for preparing these compositions and processes for the desiccation and/or defoliation of plants using the compounds I have been found.

Depending on the substitution pattern, the compounds of the formula I can contain one or more chiral centers and then exist as enantiomer or diastereomer mixtures. The invention relates both to the pure enantiomers or diastereomers and to their mixtures.

If A is hydrogen, the 3-aryluracils I can be present in the form of their agriculturally utilizable salts, the nature of the salt generally not mattering. In general, the salts of those bases are suitable in which the herbicidal action is not adversely affected in comparison with the free compound I.

Suitable basic salts are paticularly those of the alkali metals, preferably sodium and potassium salts, the alkaline earth metals, preferably calcium and magnesium salts, those of the transition metals, preferably zinc and iron salts, and also ammonium salts in which the ammonium ion, if desired, can carry one to three $C_1$–$C_4$-alkyl or hydroxy-$C_1$–$C_4$-alkyl substituents and/or a phenyl or benzyl substituent, preferably diisopropylammonium, tetramethylammonium, tetrabutylammonium, trimethylbenzylammonium and trimethyl-(2-hydroxyethyl)ammonium salts, in addition phosphonium salts, sulfonium salts such as preferably tri($C_1$–$C_4$-alkyl)-sulfonium salts, and sulfoxonium salts such as preferably tri($C_1$–$C_4$-alkyl)sulfoxonium salts.

The organic entities mentioned for the substituents $R^2$ to $R^{10}$ or as radicals on phenyl rings or heterocycles are collective terms for individual lists of the separate group members. All carbon chains, ie. all alkyl, haloalkyl, alkoxy, alkylthio, alkylsulfenyl, alkylsulfonyl, alkylcarbonyl, alkoxycarbonyl, alkenyl, alkenyloxy, alkenylcarbonyl, alkynyl, alkynyloxy, alkynylcarbonyl and alkylideneaminooxy moieties, can be straight-chain or branched. If not stated otherwise, halogenated substituents preferably carry one to five identical or different halogen atoms. The meaning of halogen is in each case fluorine, chlorine, bromine or iodine.

The following radicals further mean, for example:
$C_1$–$C_6$-alkyl and the alkyl moieties of $C_1$–$C_6$-alkoxy-$C_1$–$C_6$-alkyl and ($C_1$–$C_6$-alkoxy)carbonyl-$C_1$–$C_6$-alkyl: methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, 1,1-dimethylpropyl, 1,2-dimethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl;

$C_1$–$C_6$-haloalkyl: a $c_1$–$c_6$-alkyl radical as mentioned above, which is partially or completely substituted by fluorine, chlorine, bromine and/or iodine, ie., for example, chloromethyl, dichloromethyl, trichloromethyl, fluoromethyl, difluoromethyl, trifluoromethyl, chlorofluormethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-di-fluoroethyl, 2,2-dichloro-2-fluoroethyl, 2,2,2-trichloroethyl, pentafluoroethyl, 2-fluoropropyl,3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl or dodecafluorohexyl;

phenyl-$C_1$–$C_6$-alkyl: eg. benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 3-phenylbut-2-yl, 4-phenylbut-2-yl, 1-(phenylmethyl)eth-1-yl, 1-(phenylmethyl)-1-(methyl)-eth-1-yl or 1-(phenylmethyl)prop-1-yl, preferably benzyl, 2-phenylethyl or 2-phenyl-hex-6-yl;

$C_3$–$C_6$-alkenyl and the alkenyl moieties of $C_3$–$C_6$-alkenyloxy and ($C_3$–$C_6$-alkenyl)carbonyl: prop-1-en-1-yl, prop-2-en-1-yl, 1-methylethenyl, n-buten-1-yl, n-buten-2-yl, n-buten-3-yl, 1-methyl-prop-1-en-1-yl, 2-methyl-prop-1-en-1-yl, 1-methyl-prop-2-en-1-yl or 2-methyl-prop-2-en-1-yl, n-penten-1-yl, n-penten-2-yl, n-penten-3-yl, n-penten-4-yl, 1-methyl-but-1-en-1-yl, 2-methyl-but-1-en-1-yl, 3-methyl-but-1-en-1-yl, 1-methyl-but-2-en-1-yl, 2-methyl-but-2-en-1-yl, 3-methyl-but-2-en-1-yl, 1-methyl-but-3-en-1-yl, 2-methyl-but-3-en-1-yl, 3-methyl-but-3-en-1-yl, 1,1-dimethyl-prop-2-en-1-yl, 1,2-dimethyl-prop-1-en-1-yl, 1,2-dimethyl-prop-2-en-1-yl, 1-ethyl-prop-1-en-2-yl, 1-ethyl-prop-2-en-1-yl, n-hex-1-en-1-yl, n-hex-2-en-1-yl, n-hex-3-en-1-yl, n-hex-4-en-1-yl, n-hex-5-en-1-yl, 1-methyl-pent-1-en-1-yl, 2-methyl-pent-1-en-1-yl, 3-methyl-pent-1-en-1-yl, 4-methyl-pent-1-en-1-yl, 1-methyl-pent-2-en-1-yl, 2-methyl-pent-2-en-1-yl, 3-methyl-pent-2-en-1-yl, 4-methyl-pent-2-en-1-yl, 1-methyl-pent-3-en-1-yl, 2-methyl-pent-3-en-1-yl, 3-methyl-pent-3-en-1-yl, 4-methyl-pent-3-en-1-yl, 1-methyl-pent-4-en-1-yl, 2-methyl-pent-4-en-1-yl, 3-methyl-pent-4-en-1-yl, 4-methyl-pent-4-en-1-yl, 1,1-dimethyl-but-2-en-1-yl, 1,1-dimethyl-put-3-en-1-yl, 1,2-dimethyl-but-1-en-1-yl, 1,2-dimethyl-put-2-en-1-yl, 1,2-dimethyl-but-3-en-1-yl, 1,3-dimethyl-put-1-en-1-yl, 1,3-dimethyl-but-2-en-1-yl, 1,3-dimethyl-put-3-en-1-yl, 2,2-dimethyl-but-3-en-1-yl, 2,3-dimethyl-put-1-en-1-yl, 2,3-dimethyl-but-2-en-1-yl, 2,3-dimethyl-put-3-en-1-yl, 3,3-dimethyl-but-1-en-1-yl, 3,3-dimethyl-put-2-en-1-yl, 1-ethyl-but-1-en-1-yl, 1-ethyl-but-2-en-1-yl, 1-ethyl-but-3-en-1-yl, 2-ethyl-but-1-en-1-yl, 2-ethyl-but-2-en-1-yl, 2-ethyl-but-3-en-1-yl, 1,1,2-trimethyl-prop-2-en-1-yl, 1-ethyl-1-methyl-prop-2-en-1-yl, 1-ethyl-2-methyl-prop-1-en-1-yl or 1-ethyl-2-methyl-prop-2-en-1-yl;

$C_3$–$C_6$-alkynyl and the alkynyl moieties of $C_3$–$C_6$-alkynyloxy and ($C_3$–$C_6$-alkynyl) carbonyl: prop-1-yn-1-yl, prop-2-yn-1-yl, but-1-yn-1-yl, but-1-yn-3-yl, but-1-yn-4-yl, but-2-yn-1-yl, pent-1-in-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl;

$C_1$–$C_6$-alkoxy and the alkoxy moieties of $C_1$–$C_6$-alkoxy-$C_1$–$C_6$-alkyl, ($C_1$–$C_6$-alkoxy)carbonyl-$C_1$–$C_6$-alkyl and ($C_1$–$C_6$-alkoxy) carbonyl-$C_1$–$C_6$-alkoxy: methoxy, ethoxy, n-propoxy, 1-methylethoxy, n-butoxy, 1-methylpropoxy, 2-methylpropoxy, 1,1-dimethylethoxy, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

$C_1$–$C_6$-alkylthio: methylthio, ethylthio, n-propylthio, 1-methylethylthio, n-butylthio, 1-methylpropylthio, 2-methylpropylthio, 1,1-dimethylethylthio, n-pentylthio, 1-methylbutylthio, 2-methylbutylthio, 3-methylbutylthio, 2,2-dimethylpropylthio, 1-ethylpropylthio, n-hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio;

($C_1$–$C_6$-alkyl)carbonyl: methylcarbonyl, ethylcarbonyl, n-propylcarbonyl, 1-methylethylcarbonyl, n-butylcarbonyl, 1-methylpropylcarbonyl, 2-methylpropylcarbonyl, 1,1-dimethylethylcarbonyl, n-pentylcarbonyl, 1-methylbutylcarbonyl, 2-methylbutylcarbonyl, 3-methylbutylcarbonyl, 1,1-dimethyl-propylcarbonyl, 1,2-dimethylpropylcarbonyl, 2,2-dimethyl-propylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1- methylpropylcarbonyl or 1-ethyl-2-methylpropylcarbonyl;

$C_1$–$C_4$-alkylsulfenyl: methylsulfenyl, ethylsulfenyl, n-propylsulfenyl, 1-methylethylsulfenyl, n-butylsulfenyl, 1-methylpropylsulfenyl, 2-methylpropylsulfenyl, 1,1-dimethylpropylsulfenyl, n-pentylsulfenyl, 1-methylbutylsulfenyl, 2-methylbutylsulfenyl, 3-methylbutylsulfenyl, 2,2-dimethylpropylsulfenyl, 1-ethylpropylsulfenyl, 1,1-dimethylpropylsulfenyl, 1,2-dimethylpropylsulfenyl, n-hexylsulfenyl, 1-methylpentylsulfenyl, 2-methylpentylsulfenyl, 3-methylpentylsulfenyl, 4-methylpentylsulfenyl, 1,1-dimethylbutylsulfenyl, 1,2-dimethylbutylsulfenyl, 1,3-dimethylbutylsulfenyl, 2,2-dimethylbutylsulfenyl, 2,3-dimethylbutylsulfenyl, 3,3-dimethylbutylsulfenyl, 1-ethylbutylsulfenyl, 2-ethylbutylsulfenyl, 1,1,2-trimethylpropylsulfenyl, 1,2,2-trimethylpropylsulfenyl, 1-ethyl-1-methylpropylsulfenyl or 1-ethyl-2-methylpropylsulfenyl;

$C_1$–$C_4$-alkylsulfonyl: methylsulfonyl, ethylsulfonyl, n-propylsulfonyl, 1-methylethylsulfonyl, n-butylsulfonyl, 1-methylpropylsulfonyl, 2-methylpropylsulfonyl, 1,1-dimethylethylsulfonyl, n-pentylsulfonyl, 1-methylbutylsulfonyl, 2-methylbutylsulfonyl, 3-methylbutylsulfonyl, 2,2-dimethylpropyl-sulfonyl, 1-ethylpropylsulfonyl, 1,1-dimethylpropylsulfonyl, 1,2-dimethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-di-methylbutylsulfonyl, 1,3-dimethylbutylsulfonyl, 2,2-di-methylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl,1,2,2-trimethylpropylsulfonyl, 1-ethyl-1-methylpropylsulfonyl or 1-ethyl-2-methylpropylsulfonyl;

$C_1$–$C_6$-alkylideneaminoxy: acetylideneaminoxy, 1-propylideneaminoxy, 2-propylideneaminoxy, 1-butylideneaminoxy, 2-butylideneaminoxy or 2-hexylideneaminoxy;

$C_3$–$C_8$-cycloalkyl: cyclopropyl, cyclobutyl, cyclopentyl, cyclohexyl, cycloheptyl and cyclooctyl;

$C_3$–$C_8$-cycloalkoxy: cyclopropyloxy, cyclobutyloxy, cyclopentyloxy, cyclohexyloxy, cycloheptyloxy and cyclooctyloxy.

Examples of 3- to 7-membered heterocycles are oxiranyl, aziridinyl, oxetanyl, tetrahydrofuranyl, tetrahydrothienyl, pyrrolidinyl, isoxazolidinyl, isothiazolidinyl, pyrazolidinyl, oxazolidinyl, thiazolidinyl, imidazolidinyl, dioxolanyl such as 1,3-dioxolan-2-yl and 1,3-dioxolan-4-yl, dioxanyl such as 1,3-dioxan-2-yl und 1,3-dioxan-4-yl, dithianyl such as 1,3-dithian-2-yl, in addition 1,2,4-oxadiazolidinyl, 1,3,4-oxadiazolidinyl, 1,2,4-thiadiazolidinyl, 1,3,4-thiadiazolidinyl, 1,2,4-triazolidinyl, 1,3,4-triazolidinyl, 2,3-dihydrofuryl, 2,5-dihydrofuryl, 2,3-dihydrothienyl, 2,5-dihydrothienyl, 2,3-pyrrolinyl, 2,5-pyrrolinyl, 2,3-isoxazolinyl, 3,4-isoxazolinyl, 4,5-isoxazolinyl, 2,3-isothiazolinyl, 3,4-isothiazolinyl, 4,5-isothiazolinyl, 2,3-dihydropyrazolyl, 3,4-dihydropyrazolyl, 4,5-dihydropyrazolyl, 2,3-dihydrooxazolyl, 3,4-dihydrooxazolyl, piperidinyl, tetrahydropyridazinyl, tetrahydropyrimidinyl, tetrahydropyrazinyl, 1,3,5-tetrahydrotriazinyl and 1,2,4-tetrahydrotriazinyl, and also the following heteroaromatics:

furyl such as 2-furyl and 3-furyl, thienyl such as 2-thienyl and 3-thienyl, pyrrolyl such as 2-pyrrolyl and 3-pyrrolyl, isoxazolyl such as 3-isoxazolyl, 4-isoxazolyl and 5-isoxazolyl, isothiazolyl such as 3-isothiazolyl, 4-isothiazolyl and 5-isothiazolyl, pyrazolyl such as 1-pyrazolyl, 3-pyrazolyl and 4-pyrazolyl, oxazolyl such as 2-oxazolyl, 4-oxazolyl and 5-oxazolyl, thiazolyl such as 2-thiazolyl, 4-thiazolyl and 5-thiazolyl, imidazolyl such as 2-imidazolyl and 4-imidazolyl, oxadiazolyl such as 1,2,4-oxadiazol-3-yl, 1,2,4-oxadiazol-5-yl and 1,3,4-oxadiazol-2-yl, thiadiazolyl such as 1,2,4-thiadiazol-3-yl, 1,2,4-thiadiazol-5-yl and 1,3,4-thiadiazol-2-yl, triazolyl such as 1,2,4-triazol-1-yl, 1,2,4-triazol-3-yl and 1,2,4-triazol-4-yl, pyridinyl such as 2-pyridinyl, 3-pyridinyl and 4-pyridinyl, pyridazinyl such as 3-pyridazinyl and 4-pyridazinyl, pyrimidinyl such as 2-pyrimidinyl, 4-pyrimidinyl und 5-pyrimidinyl, in addition 2-pyrazinyl, 1,3,5-triazin-2-yl and 1,2,4-triazin-3-yl, in particular pyridyl, pyrimidyl, furanyl and thienyl.

All phenyl and heterocyclic rings are preferably unsubstituted or carry a halogen, methyl, trifluoromethyl or methoxy substituent.

With respect to the use of the compounds of the formula I according to the invention as herbicides and/or as compounds having defoliant/desiccant activity, the variables preferably have the following meanings, to be specific in each case per se alone or in combination:

A is amino or methyl;

$R^1$ is hydrogen, fluorine or chlorine, particularly preferably hydrogen or fluorine;

$R^2$ is halogen, $C_1$–$C_6$-alkyl, $C_1$–$C_6$-haloalkyl or $C_1$–$C_6$-alkylsulfonyl, particularly preferably $C_1$–$C_4$-haloalkyl, in particular trifluoromethyl, chlorodifluoromethyl and pentafluoroethyl;

$R^3$ is hydrogen or halogen;

X is oxygen or —N($R^7$)—, where $R^7$ is hydrogen or $C_1$–$C_6$-alkyl;

$Y^1$ and $y^2$ are oxygen;

Z is oxygen or —N($R^8$)—;

$R^5$, $R^6$ and $R^8$ independently of one another are hydrogen or $C_1C_6$-alkyl; or $R^6$ and $R^8$ together are a second chemical bond;

$R^4$ is hydrogen, $C_1$–$C_6$-alkyl, $C_3$–$C_8$-cycloalkyl, $C_1$–$C_6$-haloalkyl, $C_3$–$C_6$-alkenyl, $C_3$–$C_6$-alkynyl, ($C_1$–$C_6$-alkyl)carbonyl, ($C_3$–$C_6$-alkenyl)carbonyl, ($C_3$–$C_6$-alkynyl)carbonyl or $C_1$–$C_6$-alkylsulfonyl, where each of the last-mentioned 9 radicals, if desired, can additionally carry one or two substituents, in each case selected from the group consisting of halogen, nitro, cyano, hydroxyl, $C_3$–$C_8$-cycloalkyl, $C_1$–$C_6$-alkoxy, $C_3$–$C_8$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfenyl, $C_1$–$C_6$-alkylsulfonyl, $C_1$–$C_6$-alkylideneaminooxy, a 3- to 7-membered heterocyclyl, heterocyclyloxy, heterocyclylcarbonyl or heterocyclylcarbonyloxy group having one to three hetero atoms as ring members, selected from the group consisting of two oxygen atoms, two sulfur atoms and 3 nitrogen atoms, where the heterocycle can be saturated, partially or completely unsaturated or aromatic and, if desired, can carry one to three substituents, in each case selected from the group consisting of halogen, nitro, cyano, $C_1C_6$-alkyl, $C_1$–$C_6$-alkoxy, $C_1$–$C_6$-haloalkyl and ($C_1$-$C_6$-alkyl)carbonyl, a group —CO—R$^9$, —O—CO—R$^9$, —CO—OR$^9$, —O—CO—OR$^9$, —CO—SR$^9$, —O—CO—SR$^9$, —CO—N(R$^9$)R$^{10}$, —O—CO—N(R$^9$)R$^{10}$, —N(R$^9$)R$^{10}$ or —C(NR$^{11}$)—OR$^{12}$, R$^9$ being hydrogen, C$_1$–C$_6$-alkyl, C$_3$–C$_8$-cycloalkyl, C$_3$–C$_6$-alkenyl, C$_3$–C$_6$-alkynyl, C$_1$–C$_6$-alkoxy-C$_1$–C$_6$-alkyl or (C$_1$–C$_6$-alkoxy)-carbonyl-C$_1$–C$_6$-alkyl, R$^{10}$ being hydrogen, hydroxyl, C$_1$–C$_6$-alkyl, C$_3$–C$_8$-cycloalkyl or C$_1$–C$_6$-alkoxy, R$^{11}$ being C$_1$–C$_6$-alkoxy or C$_3$–C$_6$-alkenyloxy and R$^{12}$ being (C$_1$–C$_6$-alkoxy) carbonyl-C$_1$–C$_6$-alkyl.

Particularly preferably, Z is —N(R$^8$)— and R$^8$, together with R$^6$, is a second chemical bond. R$^4$ is particularly preferably:

hydrogen, C$_1$–C$_6$-alkyl, C$_3$–C$_8$-cycloalkyl, C$_3$–C$_6$-alkenyl or C$_3$–C$_6$-alkynyl, where each of the last-mentioned 4 radicals can carry one of the following substituents: halogen, nitro, cyano, hydroxyl, C$_3$–C$_8$-cycloalkyl, C$_1$–C$_6$-alkoxy, C$_3$–C$_8$-cycloalkoxy, C$_3$–C$_6$-alkenyloxy, C$_3$–C$_6$-alkynyloxy, C$_1$–C$_6$-alkoxy-C$_1$–C$_6$-alkoxy, C$_1$–C$_6$-alkylthio, C$_1$–C$_6$-alkylsulfenyl, C$_1$–C$_6$-alkylsulfonyl, C$_1$–C$_6$-alkylideneaminoxy, —CO—OR$^9$, —O—CO-OR$^9$, —CO—N(R$^9$)R$^{10}$, —O—CO—N(R$^9$)R$^{10}$ or —N(R$^9$)R$^{10}$, R$^9$ being hydrogen, C$_1$–C$_6$-alkyl, C$_3$–C$_8$-cycloalkyl, C$_3$–C$_6$-alkenyl, C$_3$–C$_6$-alkynyl, C$_1$–C$_6$-alkoxy-C$_1$–C$_6$-alkyl or (C$_1$–C$_6$-alkoxy)-carbonyl-C$_1$–C$_6$-alkyl, and R$^{10}$ being hydrogen or C$_1$–C$_6$-alkyl.

Very particularly preferred compounds Ia (=I where A=amino; R$^1$=fluorine; R$^2$=trifluoromethyl; R$^3$, R$^5$ and R$^6$=hydrogen; X, Y$^1$, Y$^2$ and Z=oxygen) are those listed in the following Table 1:

TABLE 1

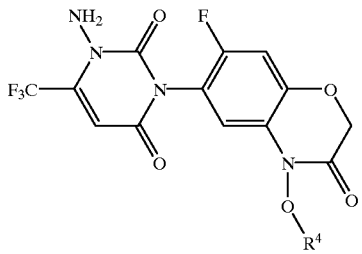

Ia

| No. | R$^4$ |
|---|---|
| Ia.01 | H |
| Ia.02 | CH$_3$ |
| Ia.03 | C$_2$H$_5$ |
| Ia.04 | n-C$_3$H$_7$ |
| Ia.05 | i-C$_3$H$_7$ |
| Ia.06 | n-C$_4$H$_9$ |
| Ia.07 | i-C$_4$H$_9$ |
| Ia.08 | s-C$_4$H$_9$ |
| Ia.09 | tert-C$_4$H$_9$ |
| Ia.10 | Cyclopropyl |
| Ia.11 | Cyclobutyl |
| Ia.12 | Cyclopentyl |
| Ia.13 | Cyclohexyl |
| Ia.14 | Cycloheptyl |
| Ia.15 | Cyclooctyl |
| Ia.16 | CH$_2$CN |
| Ia.17 | CH$_2$CH$_2$CN |
| Ia.18 | CH(CH$_3$)CN |
| Ia.19 | C(CH$_3$)$_2$CN |

TABLE 1-continued

Ia

| No. | R$^4$ |
|---|---|
| Ia.20 | C(CH$_3$)$_2$CH$_2$CN |
| Ia.21 | CH$_2$Cl |
| Ia.22 | CH$_2$CH$_2$Cl |
| Ia.23 | CH(CH$_3$)CH$_2$Cl |
| Ia.24 | CH$_2$CF$_3$ |
| Ia.25 | CHCl$_2$ |
| Ia.26 | CF$_2$Cl |
| Ia.27 | CF$_3$ |
| Ia.28 | C$_2$F$_5$ |
| Ia.29 | CF$_2$H |
| Ia.30 | CH$_2$—CH=CH$_2$ |
| Ia.31 | CH(CH$_3$)CH=CH$_2$ |
| Ia.32 | CH$_2$—CH=CH—CH$_3$ |
| Ia.33 | CH$_2$—C≡CH |
| Ia.34 | CH(CH$_3$)C≡CH |
| Ia.35 | C(CH$_3$)$_2$C≡CH |
| Ia.36 | CH$_2$—COOH |
| Ia.37 | CH$_2$—COOCH$_3$ |
| Ia.38 | CH$_2$—COOC$_2$H$_5$ |
| Ia.39 | CH$_2$—COO-n-C$_3$H$_7$ |
| Ia.40 | CH$_2$—COO-i-C$_3$H$_7$ |
| Ia.41 | CH(CH$_3$)—COOCH$_3$ |
| Ia.42 | CH(CH$_3$)—COO—C$_2$H$_5$ |
| Ia.43 | CH(CH$_3$)—COO-n-C$_3$H$_7$ |
| Ia.44 | CH(CH$_3$)—COO-i-C$_3$H$_7$ |
| Ia.45 | CH$_2$—COO—(CH$_2$)$_2$—OCH$_3$ |
| Ia.46 | CH$_2$—COO—(CH$_2$)$_2$—OCH$_3$ |
| Ia.47 | CH(CH$_3$)—COO—(CH$_2$)$_2$—OCH$_3$ |
| Ia.48 | CH(CH$_3$)—COO—(CH$_2$)$_2$—OC$_2$H$_5$ |
| Ia.49 | CH$_2$—CONH$_2$ |
| Ia.50 | CH$_2$—CONHCH$_3$ |
| Ia.51 | CH$_2$—CONHC$_2$H$_5$ |
| Ia.52 | CH$_2$—CON(CH$_3$)$_2$ |
| Ia.53 | CH(CH$_3$)—CONH$_2$ |
| Ia.54 | CH(CH$_3$)—CONHCH$_3$ |
| Ia.56 | CH(CH$_3$)—CONHC$_2$H$_5$ |
| Ia.57 | CH(CH$_3$)—CON(CH$_3$)$_2$ |
| Ia.58 | CO—CH$_3$ |
| Ia.59 | CO—C$_2$H$_5$ |
| Ia.60 | CO-i-C$_3$H$_7$ |
| Ia.61 | CO-n-C$_4$H$_9$ |
| Ia.62 | CO-cyclopropyl |
| Ia.63 | CO-cyclopentyl |
| Ia.64 | CO—CF$_3$ |
| Ia.65 | CO—OCH$_3$ |
| Ia.66 | CO—OC$_2$H$_5$ |
| Ia.67 | SO$_2$—CH$_3$ |
| Ia.68 | CH$_2$—SCH$_3$ |
| Ia.69 | (CH$_2$)$_2$—SCH$_3$ |
| Ia.70 | (CH$_2$)$_2$—SC$_2$H$_5$ |
| Ia.71 | (CH$_2$)$_2$—SO—CH$_3$ |
| Ia.72 | (CH$_2$)$_2$—SO$_2$—CH$_3$ |
| Ia.73 | (CH$_2$)$_2$—SO—CH$_3$ |
| Ia.74 | (CH$_2$)$_2$-cyclopropyl |
| Ia.76 | (CH$_2$)$_2$-cyclopentyl |
| Ia.77 | (CH$_2$)$_2$—ON=C(CH$_3$)$_2$ |
| Ia.78 | (CH$_2$)$_3$—ON=C(CH$_3$)$_2$ |
| Ia.79 | (CH$_2$)$_2$—NO$_2$ |
| Ia.80 | (CH$_2$)$_2$—NH$_2$ |
| Ia.81 | (CH$_2$)$_2$—NHCH$_3$ |
| Ia.82 | (CH$_2$)$_2$—NH(CH$_3$)$_2$ |
| Ia.83 | CH$_2$—OCH$_3$ |

TABLE 1-continued

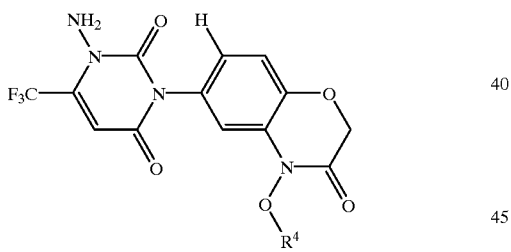

Ia

| No. | R⁴ |
|---|---|
| Ia.84 | CH(CH₃)—OCH₃ |
| Ia.85 | CH(CH₃)—OC₂H₅ |
| Ia.86 | CH(CH₃)CH₂—OCH₃ |
| Ia.87 | (CH₂)₂OH |
| Ia.88 | CH₂—OC₂H₅ |
| Ia.89 | CH₂—COO-(4-acetoxy-tetrahydrofuran-3-yl) |
| Ia.90 | CH₂—OCOCH₃ |
| Ia.91 | CH₂—OCOC₂H₅ |
| Ia.92 | CH₂—C₆H₅ |
| Ia.93 | (CH₂)₂—C₆H₅ |
| Ia.94 | CH₂-(4-Cl-C₆H₄) |
| Ia.95 | CH₂-(4-CF₃—C₆H₄) |
| Ia.96 | CH₂-(3-NO₂—C₆H₄) |
| Ia.97 | CH(CH₃)C(NOCH₃)CH₂COOCH₃ |

Very particularly preferred 1-aryluracils of the formula I are further the following:

the compounds Ib.01–Ib.97, which only differ from the corresponding compounds Ia.01–Ia.97 in that $R^1$ is hydrogen:

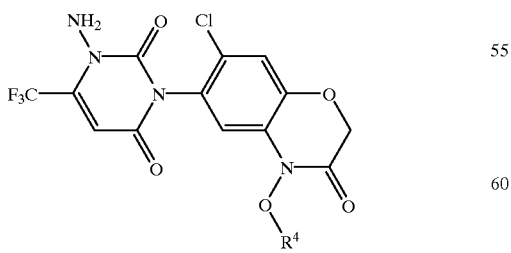

Ib the compounds Ic.01–Ic.97, which only differ from the corresponding compounds Ia.01–Ia.97 in that $R^1$ is chlorine.

Ic the compounds Id.01–Id.97, which only differ from the corresponding compounds Ia.01–Ia.97 in that A is methyl:

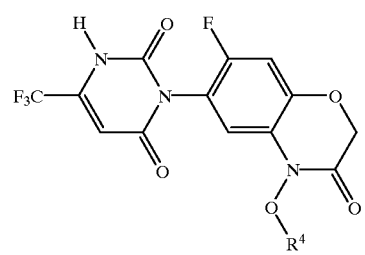

Id the compounds Ie.01–Ie.97, which only differ from the corresponding compounds Ia.01–Ia.97 in that A is hydrogen:

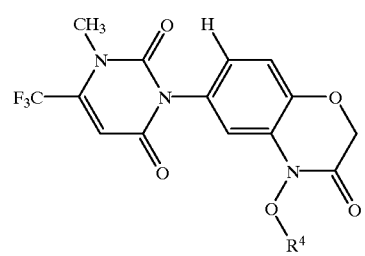

Ie the compounds If.01–If.97, which only differ from the corresponding compounds Ia.01–Ia.97 in that A is methyl and $R^1$ is hydrogen:

If the compounds Ig.01–Ig.97, which only differ from the corresponding compounds Ia.01–Ia.97 in that A and $R^1$ are hydrogen:

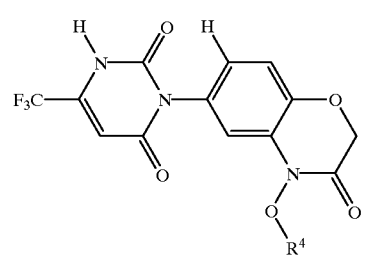

Ig the compounds Ih.01–Ih.97, which only differ from the corresponding compounds Ia.01–Ia.97 in that A is methyl and $R^1$ is chlorine:

the compounds Ii.01–Ii.97, which only differ from the corresponding compounds Ia.01–Ia.97 in that $R^1$ is chlorine and A is hydrogen:

the compounds Ik.01–Ik.97, which only differ from the corresponding compounds Ia.01–Ia.97 in that X is —NH—:

the compounds Il.01–Il.97, which only differ from the corresponding compounds Ia.01–Ia.97 in that X is —N— and A is methyl:

the compounds Im.01–Im.97, which only differ from the corresponding compounds Ia.01–Ia.97 in that X is —N— and A is hydrogen:

the compounds In.01–In.97, which only differ from the corresponding compounds Ia.01–Ia.97 in that X is —N— and $R^1$ is chlorine:

the compounds Io.01–Io.97, which only differ from the corresponding compounds Ia.01–Ia.97 in that X is —N—, A is methyl and $R^1$ is hydrogen:

the compounds Ip.01–Ip.97, which only differ from the corresponding compounds Ia.01–Ia.97 in that X is —N—, A is methyl and $R^1$ is chlorine:

the compounds Iq.01–Iq.97, which only differ from the corresponding compounds Ia.01–Ia.97 in that Z is —N—:

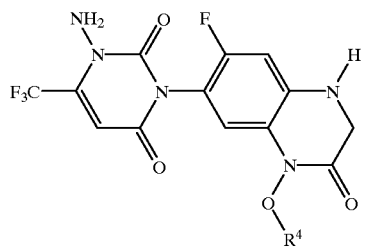

Iq the compounds Ir.01–Ir.97, which only differ from the corresponding compounds Ia.01–Ia.97 in that Z is —N— and A is methyl:

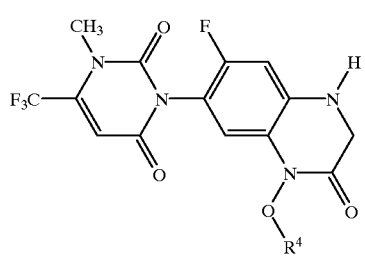

Ir the compounds Is.01–Is.97, which only differ from the corresponding compounds Ia.01–Ia.97 in that Z is —N— and A is hydrogen:

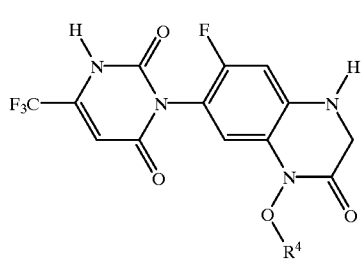

Is the compounds Iβ.01–Iβ.97, which only differ from the corresponding compounds Ia.01–Ia.97 in that Z is —N—, and $R^1$ is chlorine:

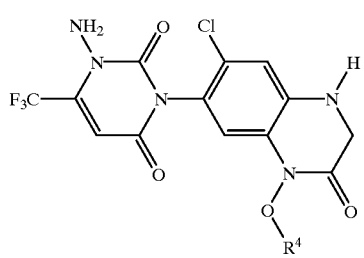

Iβ the compounds It.01–It.97, which only differ from the corresponding compounds Ia.01–Ia.97 in that Z is —N—, A is methyl and $R^1$ is hydrogen:

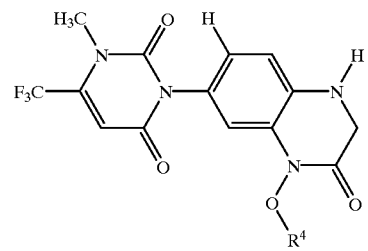

It the compounds Iu.01–Iu.97, which only differ from the corresponding compounds Ia.01–Ia.97 in that Z is —N—, A is methyl and $R^1$ is chlorine:

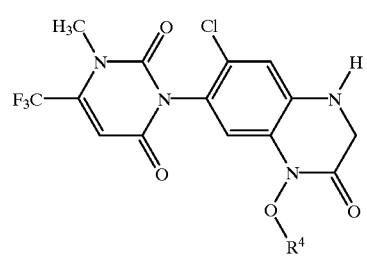

Iu the compounds Iv.01–Iv.97, which only differ from the corresponding compounds Ia.01–Ia.97 in that X and Z are both —N—:

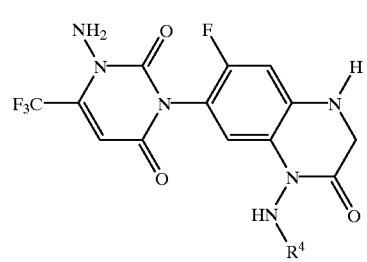

Iv the compounds Iw.01–Iw.97, which only differ from the corresponding compounds Ia.01–Ia.97 in that X and Z are both —N— and A is methyl:

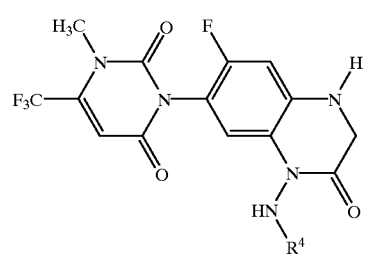

Iw the compounds Ix.01–Ix.97, which only differ from the corresponding compounds Ia.01–Ia.97 in that X and Z are both —N— and A is hydrogen:

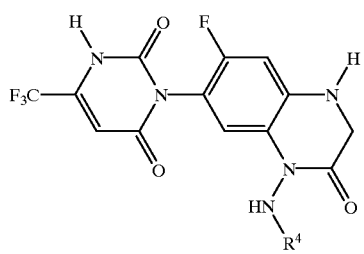

the compounds Iy.01–Iy.97, which only differ from the corresponding compounds Ia.01–Ia.97 in that X and Z are both —N— and R¹ is chlorine:

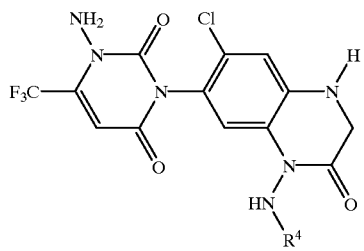

the compounds IZ.01–IZ.97, which only differ from the corresponding compounds Ia.01–Ia.97 in that X and Z are both —N—, A is methyl and R¹ is hydrogen:

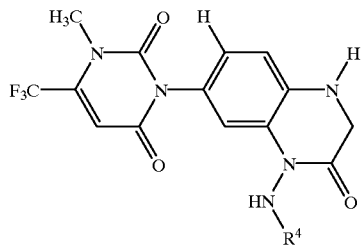

the compounds IΨ.01–IΨ.97, which only differ from the corresponding compounds Ia.01–Ia.97 in that X and Z are both —N—, A is methyl and R¹ is chlorine:

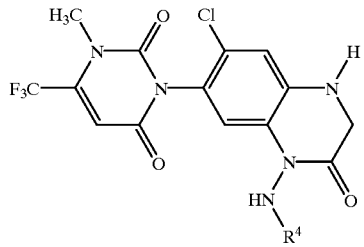

The 3-aryluracils of the formula I can be obtained in various ways, for example by one of the following processes:

Process A)

Cyclization of an enamino ester of the formula IV or of an enamine carboxylate of the formula V in the presence of a base:

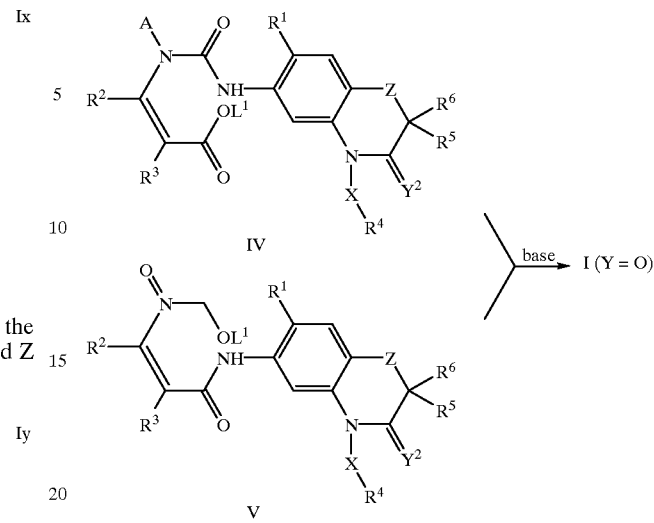

$L^1$ is lower alkyl, preferably $C_1$–$C_4$-alkyl, or phenyl.

As a rule, cyclization is carried out in an inert organic solvent or diluent which is aprotic, for example in an aliphatic or cyclic ether such as 1,2-dimethoxyethane, tetrahydrofuran or dioxane, in an aromatic such as benzene or toluene or in a polar solvent such as dimethylformamide or dimethyl sulfoxide. Mixtures of polar solvent and a hydrocarbon such as n-hexane are also suitable. Depending on the starting compound, water may also be suitable as a diluent.

Suitable bases are preferably alkali metal alkoxides, in particular the sodium alkoxides, alkali metal hydroxides, in particular sodium hydroxide and potassium hydroxide, alkali metal carbonates, in particular sodium carbonate and potassium carbonate, and metal hydrides, in particular sodium hydride. When using sodium hydride as a base, it has proven advantageous to work in an aliphatic or cyclic ether, in dimethylformamide or in dimethyl sulfoxide.

Normally, 0.5- to 2-times the molar amount of base, based on the amount of IV or V, is adequate for the success of the reaction.

In general, the reaction temperature is from −78° C. to the boiling point of the respective reaction mixture, in particular −60 to 60° C.

If A in formula III or IV is hydrogen, the product is obtained as a metal salt, the metal corresponding to the cation of the base used. The salt can be isolated and purified in a manner known per se or, if desired, converted by means of acid into the free compound I where A=hydrogen.

Process B)

Methylation of a compound I in which A is hydrogen, in the presence of a base:

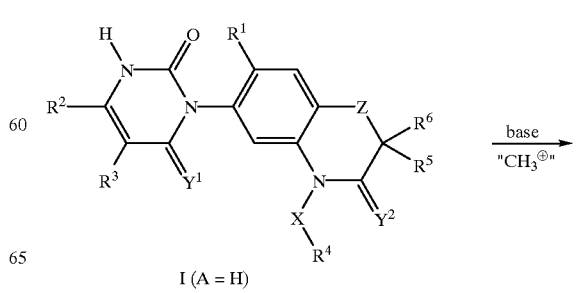

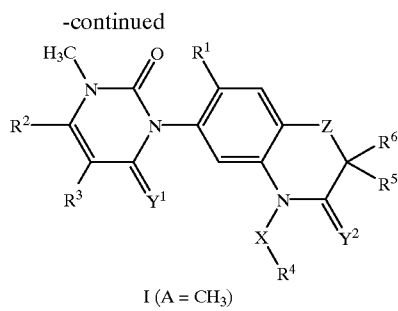

I (A = CH₃)

Suitable methylating agents are, for example, methyl halides, preferably methyl chloride, iodide or bromide, and also dimethyl sulfate, methyl methanesulfonate (methyl mesylate), methyl benzenesulfonate, methyl p-toluenesulfonate (methyl tosylate), methyl p-bromobenzenesulfonate (methyl brosylate), methyl trifluoromethanesulfonate (methyl triflate) and diazomethane.

As a rule, the reaction is carried out in an inert organic solvent, for example in a protic solvent such as the lower alcohols, preferably in ethanol, if appropriate as a mixture with water, or in an aprotic solvent, eg. in an aliphatic or cyclic ether, preferably in 1,2-dimethoxyethane, tetrahydrofuran or dioxane, in an aliphatic ketone, preferably in acetone, in an amide, preferably in dimethylformamide, in a sulfoxide, preferably in dimethyl sulfoxide, in a urea such as tetramethylurea or 1,3-dimethyltetra-hydro-2(1H)-pyrimidinone, in a carboxylic acid ester such as ethyl acetate, or in a halogenated aliphatic or aromatic hydrocarbon such as dichloromethane or chlorobenzene.

Suitable bases are inorganic bases, eg. carbonates such as sodium carbonate and potassium carbonate, hydrogen carbonates such as sodium and potassium hydrogen carbonate, or alkali metal hydrides such as sodium hydride and potassium hydride, and also organic bases, eg. amines such as triethylamine, pyridine and N,N-diethylaniline, or alkali metal alkoxides such as sodium methoxide, sodium ethoxide and potassium tert-butoxide.

The amount of base and methylating agent is preferably in each case 0.5- to 2-times the molar amount, based on the amount of starting compound.

In general, the reaction temperature is from −78° C. to the boiling point of the reaction mixture, in particular −60 to 60° C.

A preferred variant consists in methylating the salt of I obtained from the cyclization of IV (A=H) or V (A=H) as in process A) without isolation from the reaction mixture which can additionally contain excess base, eg. sodium hydride, sodium alkoxide or sodium carbonate.

If they cannot be prepared directly by the cyclization under basic conditions described as method A), the salts of those compounds I in which A is hydrogen can also be obtained in a manner known per se from the products of method A. For this purpose, the aqueous solution of an inorganic or organic base, for example, is treated with the substituted 3-aryluracil I in which A is hydrogen. Salt formation normally takes place at an adequate rate even at 20–25° C.

It is particularly advantageous to prepare the sodium salt by dissolving the 3-aryluracil I (A=hydrogen) in aqueous sodium hydroxide solution at 20–25° C., approximately equivalent amounts of 3-aryluracil and sodium hydroxide being employed. The salt of the 3-aryluracil can then be isolated, for example, by precipitating with a suitable inert solvent or by evaporating the solvent.

Salts of the 3-aryluracils whose metal ion is not an alkali metal ion can customarily be prepared by double decomposition of the corresponding alkali metal salt in aqueous solution. In this manner, for example, 3-aryluracil metal salts which are insoluble in water can be prepared.

Process C)

Reaction of a 3-aryluracil of the formula I, where A is hydrogen, with an electrophilic aminating reagent in the presence of a base:

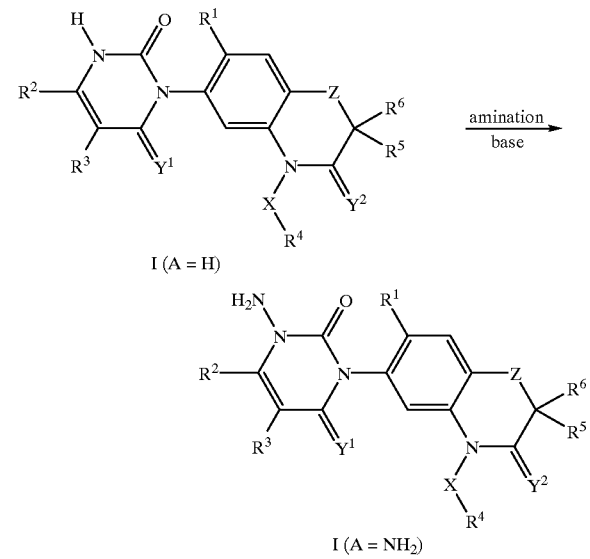

Until now, 2,4-dinitrophenoxyamine has proven particularly suitable as an aminating reagent, but hydroxylamine-O-sulfonic acid (HOSA), for example, can also be used, which is already known from the literature as an aminating reagent (cf., for example, E. Hofer et al., Synthesis 1983, 466; W. Friedrichsen et al., Heterocycles 20 (1983) 1271; H. Hart et al., Tetrahedron Lett. 2 (1984) 2073; B. Vercek et al., Monatsh. Chem. 114 (1983) 789; G. Sosnousky et al., Z. Naturforsch. 38 (1983) 884; R.S. Atkinson et al., J. Chem. Soc. Perkin Trans. 1987, 2787).

The amination can be carried out in a manner known per se (see, for example, T. Sheradsky, Tetrahedron Lett. 1968, 1909; M. P. Wentland et al., J. Med. Chem. 21 (1984) 1103 and in particular EP-A 240 194, EP-A 476 697 and EP-A 517 181, where the amination of uracils is described).

Normally, the reaction is carried out in a polar solvent, for example in dimethylformamide, N-methylpyrrolidone, dimethyl sulfoxide or in ethyl acetate, which has previously proven particularly suitable.

Suitable bases are, for example, alkali metal carbonates such as potassium carbonate, alkali metal alkoxides such as sodium methoxide and potassium tert-butoxide or alkali metal hydrides such as sodium hydride.

The amount of base and aminating agent is preferably in each case 0.5- to 2-times the molar amount, based on the amount of starting compound.

Depending on the meaning of R⁴, it may be necessary to protect this substituent from amination in a manner known per se. This is particularly advisable if R⁴ is hydrogen.

Process D)

Sulfurization of a 3-aryluracil of the formula I where Y¹=oxygen:

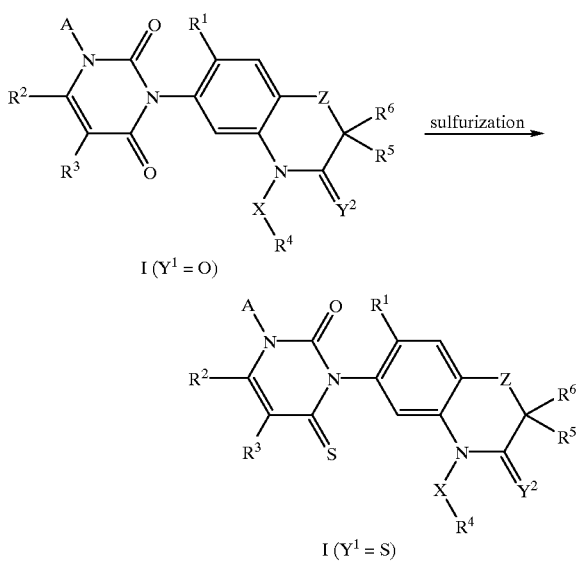

I (Y¹ = O)

I (Y¹ = S)

Sulfurization is carried out as a rule in an inert solvent or diluent, for example in an aromatic hydrocarbon such as toluene or the xylenes, in an ether such as diethyl ether, 1,2-dimethoxyehtane or tetrahydrofuran, or in an organic amine such as pyridine.

A particularly highly suitable sulfurization reagent is phosphorus(V) sulfide or 2,4-bis(4-methoxyphenyl)-1,3,2,4-dithiadiphosphetane-2,4-dithione (Lawesson's reagent).

Customarily, 1- to 5-times the molar amount, based on the starting compound to be sulfurized, is adequate for a substantially complete reaction.

The reaction temperature is normally from 20 to 200° C., preferably 40° C. up to the boiling point of the reaction mixture.

During the sulfurization of starting compounds in which $Y^1$ and $Y^2$ are oxygen, products both with $Y^1$=sulfur and with $Y^2$=sulfur can be formed. The desired pure valuable products in each case can then be isolated from the reaction mixtures, which can also additionally contain starting material, customarily with the aid of conventional separation techniques such as crystallization and chromatography.

Process E)

Alkylation of a 3-aryluracil of the formula I in which $R^4$ is hydrogen, in the presence of a base:

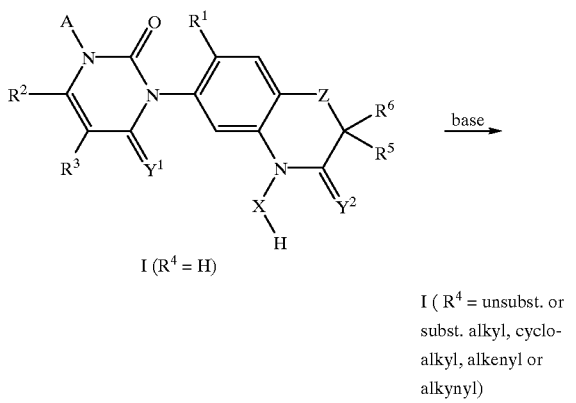

I (R⁴ = H)

I ( R⁴ = unsubst. or subst. alkyl, cycloalkyl, alkenyl or alkynyl)

Alkylation can be performed, for example, using the halide, preferably the chloride or bromide, the sulfate, sulfonate, preferably the methanesulfonate (mesylate), benzenesulfonate, p-toluenesulfonate (tosylate), p-bromobenzenesulfonate (brosylate), the trifluoromethanesulfonate (triflate) or the diazo compound of an unsubstituted or substituted alkane, cycloalkane, haloalkane, alkene or alkyne.

Normally, the reaction is carried out in an inert organic solvent, both protic solvents, such as the lower alcohols, preferably ethanol or a mixture of ethanol and water, and aprotic solvents, eg. aliphatic and cyclic ethers such as 1,2-dimethoxyethane, tetrahydrofuran and dioxane, aliphatic ketones such as acetone, amides such as dimethylformamide, sulfoxides such as dimethyl sulfoxide, ureas such as tetramethylurea and 1,3-dimethyltetrahydro-2 (1H)-pyrimidinone, carboxylic acid esters such as ethyl acetate, or halogenated aliphatic or aromatic hydrocarbons such as dichloromethane and chlorobenzene, being suitable.

Suitable bases are either inorganic bases, eg. alkali metal carbonates such as sodium carbonate and potassium carbonate, alkali metal hydrogen carbonates such as sodium and potassium hydrogen carbonate, or alkali metal hydrides such as sodium hydride and potassium hydride, and organic bases, eg. amines such as tri-ethylamine, pyridine and N,N-diethylaniline, or alkali metal alkoxides such as sodium methoxide or ethoxide and potassium tert-butoxide.

The amount of base and alkylating agent is preferably 0.5- to 2-times the molar amount, based on the amount of I where $R^4$=hydrogen.

In general, a reaction temperature from –78° C. to the boiling point of the reaction mixture is recommended, in particular from –60 to 60° C.

Possible regioselectivity problems in the case of starting compounds where A=hydrogen can be avoided in a manner known per se (use of 2 equivalents of base, introduction of a protective group etc.).

Process F)

Acylation of a 3-aryluracil of the formula I, where $R^4$ is hydrogen, using a suitable acylating agent:

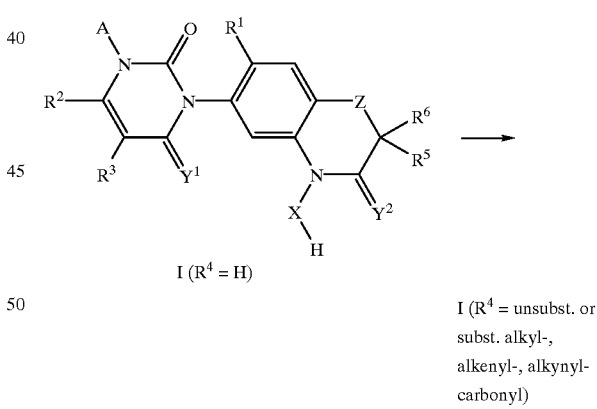

I (R⁴ = H)

I (R⁴ = unsubst. or subst. alkyl-, alkenyl-, alkynyl-carbonyl)

Suitable acylating agents are, for example, the acid halides, in particular the acid chlorides, the anhydrides, isocyanates or sulfonyl chlorides of alkane-, alkene- or alkynecarboxylic acids. However, the free acids or their anhydrides are also suitable if the reaction is then carried out in the presence of a condensing agent such as carbonyldiimidazole and dicyclohexylcarbodiimide.

As a rule, the reaction is carried out in an inert organic solvent or diluent which is preferably aprotic, eg. in an aliphatic or cyclic ether such as 1,2-dimethoxyethane, tetrahydrofuran or dioxane, an aliphatic ketone such as acetone, an amide such as dimethylformamide, a urea such as tetramethylurea or 1,3-dimethyltetrahydro-2(1H)-pyrimidinone, a carboxylic acid ester such as ethyl acetate, or an aliphatic or aromatic halohydrocarbon such as dichloromethane or chlorobenzene.

With respect to suitable bases, the quantitative ratios and the reaction temperature, reference may be made to the details under process E).

Process G)

Halogenation of a 3-aryluracil of the formula I, in which $R^3$ is hydrogen:

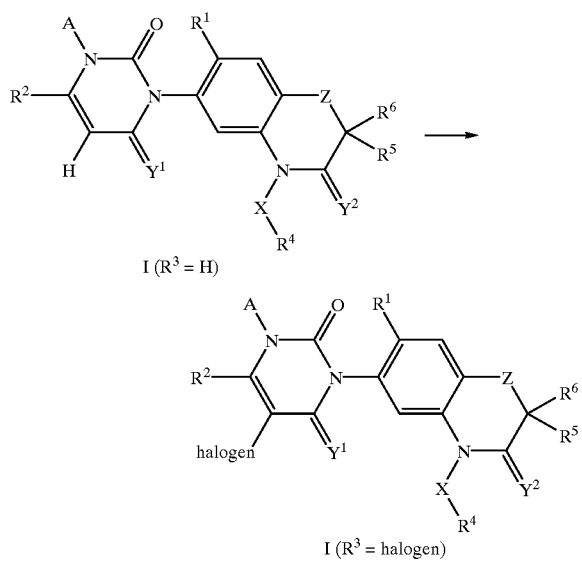

I ($R^3$ = H)

I ($R^3$ = halogen)

Halogenation is carried out as a rule in an inert organic solvent or diluent. Suitable aliphatic carboxylic acids for chlorination and bromination are, for example, those such as acetic acid, or chlorinated aliphatic hydrocarbons such as methylene chloride, chloroform and carbon tetrachloride. For iodination, low-boiling aliphatic carboxylic acids such as acetic acid are particularly preferred.

For chlorination and bromination, elemental chlorine and bromine are particularly suitable, or sulfuryl chloride or sulfuryl bromide, at a reaction temperature of preferably from 0 to 60° C., in particular 10 to 30° C.

If desired, the chlorination and bromination can be carried out in the presence of an acid acceptor, sodium acetate and tertiary amines such as triethylamine, dimethylaniline and pyridine being particularly preferred.

Elemental iodine is particularly preferred as an iodinating agent, in this case the reaction temperature being from about 0 to 110° C., preferably 10 to 30° C.

Iodination proceeds particularly advantageously in the presence of a mineral acid such as fuming nitric acid.

The amount of halogenating agent is not critical; equimolar amounts of halogenating agent or an excess of up to approximately 200 mol % are normally used, based on the starting compound (I where $R^4$=hydrogen).

Excess iodine can be removed, for example, after the reaction, by means of saturated aqueous sodium hydrogen sulfite solution.

Process H)

Amination of a heterocyclic compound of the formula VI in the presence of a base:

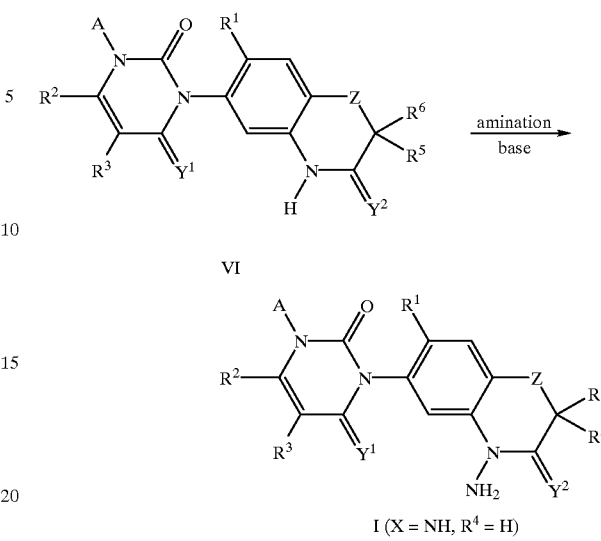

VI

I (X = NH, $R^4$ = H)

With respect to more detailed information for carrying out the process reference may be made to the details under process C).;

When using VI where A=hydrogen, in addition to the desired valuable products I (where $XR^4=NH_2$), compounds VI and/or I where A=amino can also be obtained. In these cases, it is recommended to influence the course of the reaction by means of methods which are conventional for this purpose (use of 2 equivalents of base, introduction of a protective group etc.) such that the desired product is mainly formed.

Process K)

Reduction of nitro compounds of the formula VII to hydroxylamines VIII and subsequent cyclization of VIII to I:

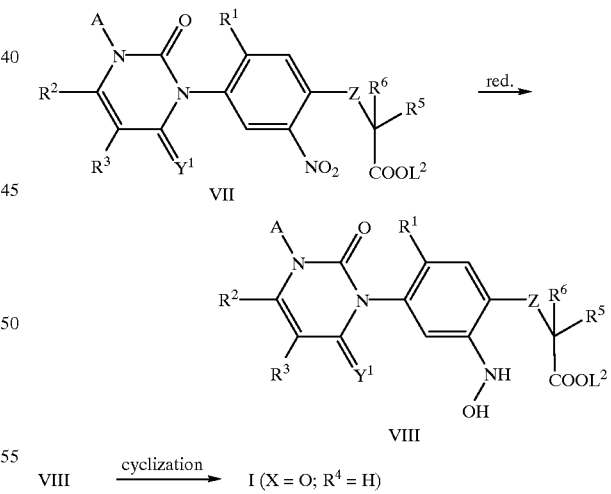

VIII $\xrightarrow{\text{cyclization}}$ I (X = O; $R^4$ = H)

$L^2$ is lower alkyl, preferably $C_1$–$C_4$-alkyl or phenyl.

For the reduction of VII, suitable reductants are those which are customary, such as tin(II) salts and iron or preferably molecular hydrogen in the presence of a catalyst such as platinum on carbon.

When using hydrogen, it is particularly advisable to work in a tertiary amine such as N-methylmorpholine as solvent.

Expediently, the reaction is carried out at a hydrogen pressure from normal pressure up to an overpressure of 10 bar.

In general, the reduction takes place at temperatures from −5 to +50° C.

The hydroxylamines VIII are novel. Their cyclization to I often takes place even at only slightly elevated temperatures, as are customary for the concentration of reaction solutions. It is therefore particularly expedient to reduce VII and to cyclize the product VIII without isolation from the reaction mixture.

The compounds I obtained can then be isolated and purified by a method known per se.

The enamino esters of the formula IV are novel. Their preparation can be carried out by methods known per se, eg. by one of the following processes:

L):

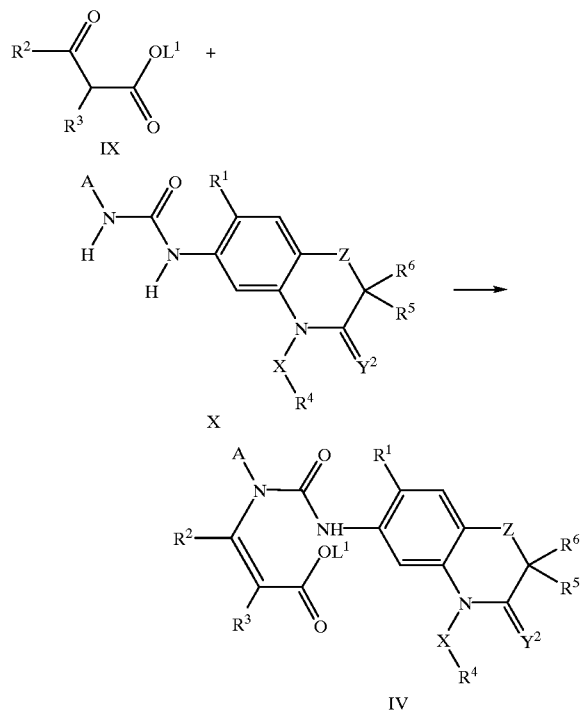

Preferably, the reaction is carried out under essentially anhydrous conditions in an inert solvent or diluent, particularly preferably in the presence of an acidic or basic catalyst.

Suitable solvents or diluents are, in particular, organic solvents which are azeotropically miscible with water, for example aromatics such as benzene, toluene and o-, m- or p-xylene, halogenated hydrocarbons such as methylene chloride, chloroform, carbon tetrachloride and chlorobenzene, aliphatic and cyclic ethers such as 1,2-dimethoxyethane, tetrahydrofuran and dioxane, or cyclohexane, but also alcohols such as methanol and ethanol.

Suitable acidic catalysts are preferably strong mineral acids such as sulfuric acid and hydrochloric acid, phosphorus-containing acids such as orthophosphoric acid and polyphosphoric acid, organic acids such as p-toluenesulfonic acid and also acidic cation exchangers such as Amberlyst 15 (Fluka).

Suitable basic catalysts are, for example, metal hydrides such as sodium hydride, and particularly preferably metal alkoxides such as sodium methoxide and ethoxide.

Expediently, IX and the β-keto ester X are employed in an approximately stoichiometric ratio or the reaction is carried out using a small excess of one or the other component, up to approximately 10 mol %.

Normally, an amount of catalyst of from 0.5 to 2 mol %, based on the amount of one starting material, is adequate.

In general, the reaction procedure is carried out at a temperature from 60 to 120° C., for rapid removal of resulting water preferably at the boiling point of the reaction mixture.

M):

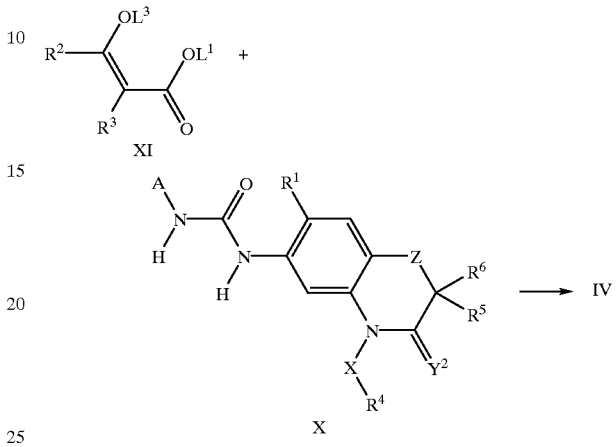

$L^3$ is $C_1$–$C_4$-alkyl or phenyl.

This reaction can be carried out, for example, in an inert, water-miscible organic solvent, for example an aliphatic or cyclic ether such as 1,2-dimethoxyethane, tetrahydrofuran or dioxane, or a lower alcohol, in particular ethanol, the reaction temperature normally being from 50 to 10° C., preferably the boiling point of the reaction mixture.

The reaction, however, can also be carried out in an aromatic diluent such as benzene, toluene or o-, m- or p-xylene, in this case the addition either of an acidic catalyst such as hydrochloric acid or p-toluenesulfonic acid or of a base, eg. an alkali metal alkoxide such as sodium methoxide or sodium ethoxide, being advisable. In this variant too, the reaction temperature is normally from 50 to 100° C., but preferably 60 to 80° C.

With respect to the quantitative ratios, the details for method L) apply.

N):

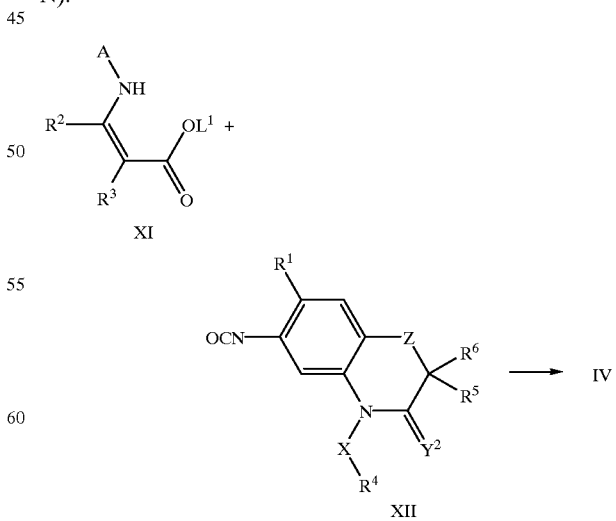

The reaction is expediently carried out in the presence of an essentially anhydrous aprotic organic solvent or diluent, for example of an aliphatic or cyclic ether such as diethyl ether, 1,2-dimethoxyethane, tetrahydrofuran or dioxane, of an aliphatic or aromatic hydrocarbon such as n-hexane, benzene, toluene or o-, m- or p-xylene, of a halogenated, aliphatic hydrocarbon such as methylene chloride, chloroform, carbon tetrachloride, 1,2-dichloroethane or chlorobenzene, of an aprotic, polar solvent such as dimethylformamide, hexamethylphosphoramide or dimethyl sulfoxide, or of a mixture of these.

If desired, the reaction can also be carried out in the presence of a metal hydride base such as sodium or potassium hydride, of an alkali metal or alkaline earth metal alkoxide such as sodium methoxide or ethoxide or potassium tert-butoxide, or of an organic tertiary base such as triethylamine or pyridine, where the organic base can simultaneously serve as a solvent.

Expediently, the starting materials are employed in a stoichiometric ratio or the reaction is carried out using a small excess of one or the other component of up to approximately 10 mol %. If the reaction is carried out without solvent in the presence of an organic base, the latter is present in a relatively large excess.

The reaction temperature is preferably from −80 to 50° C., in particular −60 to 30° C.

In a particularly preferred embodiment, the enamino ester IV obtained is converted directly (ie. in situ) into the corresponding valuable product I according to process A) using excess base.

Possible by-products (eg. C-alkylation products in the case of compounds in which $R^3$ is hydrogen) can be removed using customary separation processes such as crystallization and chromatography.

O):

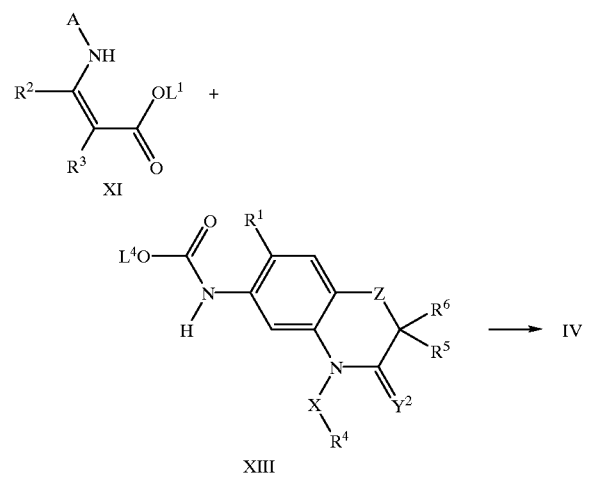

$L^4$ is $C_1$–$C_4$-alkyl or phenyl.

This reaction is expediently carried out in an aprotic, polar solvent or diluent such as dimethylformamide, 2-butanone, dimethyl sulfoxide or acetonitrile, to be specific advantageously in the presence of a base, for example of an alkali metal or alkaline earth metal alkoxide, in particular of a sodium alkoxide such as sodium methoxide, of an alkali metal or alkaline earth metal carbonate, in particular sodium carbonate, or of an alkali metal hydride such as lithium or sodium hydride.

Normally, 1- to 2-times the molar amount of base, based on the amount of XI or XIII, is adequate.

The reaction temperature is in general from 80 to 180° C., preferably the boiling point of the reaction mixture.

With respect to the quantitative ratios of the starting compounds, the details for method L) apply.

In a particularly preferred embodiment, a sodium alkoxide is used as a base and the alcohol formed in the course of the reaction is continuously distilled off. The enamino esters IV prepared in this manner can be cyclized to a salt of the 3-aryluracils I according to process A) without isolation from the reaction mixture.

P):

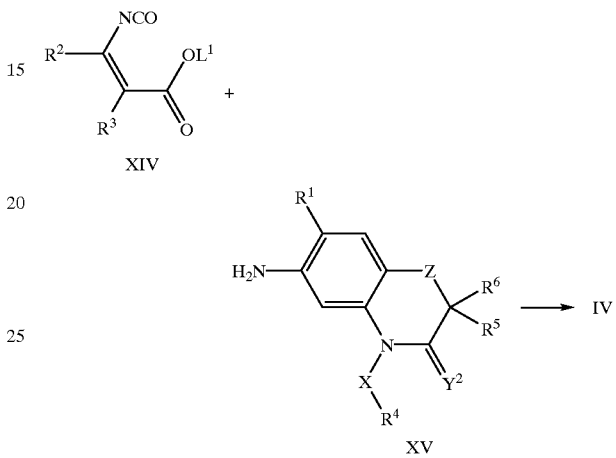

This reaction is expediently carried out in an essentially anhydrous, aprotic organic solvent or diluent, for example in the presence of an aliphatic or cyclic ether such as diethyl ether, 1,2-dimethoxyethane, tetrahydrofuran or dioxane, of an aliphatic or aromatic hydrocarbon such as n-hexane, benzene, toluene or o-, m- or p-xylene, of a halogenated, aliphatic hydrocarbon such as methylene chloride, chloroform, carbon tetrachloride, 1,2-dichloroethane or chlorobenzene, of an aprotic, polar solvent such as dimethylformamide, hexamethylphosphoramide or dimethyl sulfoxide, or of a mixture of these.

If desired, the reaction can be carried out in the presence of a metal hydride base such as sodium or potassium hydride, of an alkali metal or alkaline earth metal alkoxide such as sodium methoxide or ethoxide or potassium tert-butoxide, or of an organic nitrogen base such as triethylamine or pyridine, where the organic base can simultaneously serve as a solvent.

Expediently, the starting materials are employed in stoichiometric amounts or one of the components is used in an excess of up to approximately 20 mol %. If the reaction is carried out without solvent in the presence of an organic base, the latter is advantageously present in an even greater excess.

The reaction temperature is in general from −80 to 150° C., preferably −30° C. to the boiling point of the respective reaction mixure.

The enamine carboxylates of the formula V are also novel; they too can be prepared in a manner known per se, for example from the aniline derivatives of the formula XV according to the following reaction scheme:

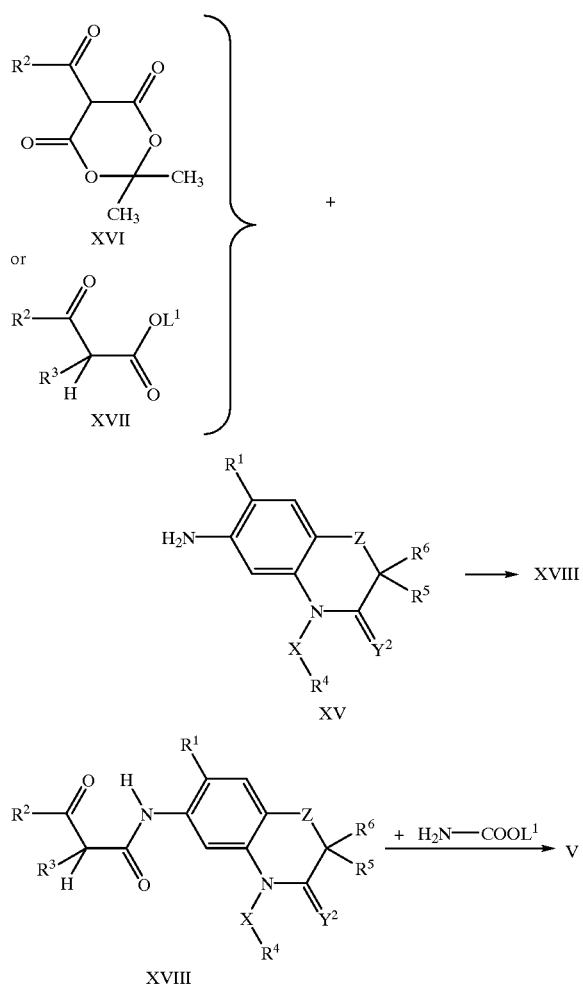

The reaction of XV with XVI is preferably carried out in an anhydrous inert aprotic solvent, for example a halogenated hydrocarbon such as methylene chloride, chloroform, carbon tetrachloride or chlorobenzene, an aromatic hydrocarbon such as benzene, toluene or o-, m- or p-xylene, or an aliphatic or cyclic ether such as diethyl ether, dibutyl ether, 1,2-dimethoxyethane, tetrahydrofuran or dioxane.

The reaction temperature in this reaction (of XV with XVI) is in general from approximately 70 to 140° C., in particular 100 to 120° C.

The reaction of XV with XVII is an aminolysis which as a rule is carried out either without solvent [cf., for example, J. Soc. Dyes Col. 42 (1926), 81, Ber. 64 (1931), 970; Org. Synth., Coll. Vol. IV (1963), 80 and J.A.C.S. 70 (1948), 2402] or in an inert anhydrous solvent/diluent, in particular in an aprotic solvent, for example in an aromatic such as toluene or o-, m- or p-xylene or a halogenated aromatic such as chlorobenzene.

In this context, working in the presence of a basic catalyst, for example of a relatively high-boiling amine [see, for example, Helv. Chim. Acta 11 (1928), 779 and U.S. Pat. No. 2,416,738] or pyridine, is recommended.

The reaction temperature is preferably from about 20 to 160° C.

Expediently, the starting compounds are in each case employed in approximately stoichiometric amounts or the reaction is carried out using a small excess of one or the other component, up to approximately 10 mol %. If the reaction is carried out in the 15 presence of a basic catalyst, normally an amount of catalyst of from 0.5 to 200 mol %, based on the amount of one of the starting materials, is adequate.

The subsequent reaction of the compounds of the formula XVIII prepared in this way with the amine $H_2N—COOL^1$ is advantageously carried out in a largely anhydrous solvent/diluent at normal pressure, particularly preferably in the presence of an acidic catalyst.

Suitable solvents/diluents are in particular organic liquids which are azeotropically miscible with water, for example aromatics such as benzene, toluene and o-, m- or p-xylene or halogenated hydrocarbons such as carbon tetrachloride and chlorobenzene.

Suitable catalysts are in particular strong mineral acids such as sulfuric acid, organic acids such as p-toluenesulfonic acid, phosphorus-containing acids such as orthophosphoric acid and polyphosphoric acid or acidic cation exchangers such as Amberlyst 15 (Fluka).

In general, the reaction temperature is from approximately 70 to 150° C.; for the rapid removal of the resulting water of reaction, however, the reaction is expediently carried out at the boiling point of the respective reaction mixture.

The compounds of the formulae X, XII and XIII are also novel. They too can be prepared in a manner known per se, particularly advantageously from compounds of the formula XV by:

Q) Phosgenation of compounds of the formula XV and hydrolysis of the products XII with ammonia (derivatives):

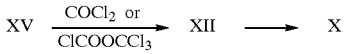

The process can be carried out in an inert, essentially anhydrous solvent/diluent or without solvent. The compounds XV are in this case preferably reacted with phosgene or trichloromethyl chloroformate.

Suitable solvents/diluents are in particular aprotic, organic solvents, for example aromatics such as toluene and o-, m- or p-xylene, halogenated hydrocarbons such as methylene chloride, chloroform, 1,2-dichloroethane and chlorobenzene, alipahatic or cyclic ethers such as 1,2-dimethoxyethane, tetrahydrofuran and dioxane, or esters such as ethyl acetate, as well as mixtures of these solvents.

Depending on the aniline derivative XV employed, the addition of a base such as triethylamine may be advantageous, for example in a 0.5- to 2-times molar amount, based on the amount of XV.

The phenyl isocyanates XII are customarily formed at reaction temperatures from 50° C. to the boiling point of the reaction mixture; they can then be reacted with ammonia or a reactive derivative of ammonia to give the phenylurea derivatives X.

R) Reaction with alkali metal cyanates:

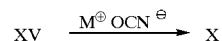

$M^⊕$ is the equivalent of a metal ion, in particular an alkali metal ion such as sodium or potassium.

The reaction is carried out as a rule in an inert solvent/diluent, for example in an aromatic hydrocarbon such as toluene or the xylenes, in an aliphatic or cyclic ether such as tetrahydrofuran or dioxane, in a lower alcohol such as methanol or ethanol, in water or in a mixture of these.

The amount of cyanate is not critical; for complete reaction, at least equimolar amounts of aniline derivative XV and cyanate are needed, but an excess of cyanate, of up to approximately 100 mol %, can also offer advantages.

The reaction temperature is in general from 0° C. to the boiling point of the reaction mixture.

S) Reaction with esters $L^4O—CO—L^5$:

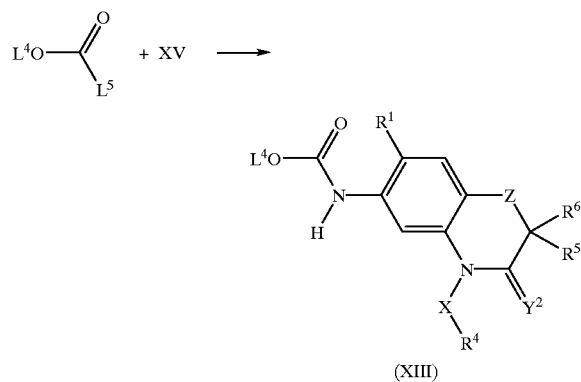

$L^5$ is halogen, preferably chlorine or bromine, $C_1$–$C_4$-alkoxy or phenoxy.

Suitable solvents/diluents are, for example, aromatic hydrocarbons such as toluene and the xylenes, halogenated hydrocarbons such as methylene chloride, chloroform, 1,2-dichloroethane and chlorobenzene, aliphatic or cyclic ethers such as 1,2-dimethoxyethane, tetrahydrofuran and dioxane, esters such as ethyl acetate, alcohols such as methanol and ethanol, or water or mixtures of an organic solvent and water.

Preferably, the reaction is performed in the presence of a base, eg. of an alkali metal hydroxide, carbonate or alkoxide such as sodium hydroxide, carbonate, methoxide or ethoxide, or of a tertiary amine such as pyridine or triethylamine.

If desired, a catalyst, eg. a Lewis acid such as antimony trichloride, can also be added.

Expediently, the starting compounds and the base are employed in approximately stoichiometric amounts, but one or the other component can also be present in an excess of up to about 100 mol %.

In general, the amount of catalyst is from 1 to 50 mol %, preferably 2 to 30 mol %, based on the amount of aniline derivative XV employed.

The reaction is normally carried out at reaction temperatures from −40° C. up to the boiling point of the reaction mixture.

The starting compounds of the formulae VI and VII are known or can be prepared in a manner known per se (cf., for example, EP-A 420 194, EP-A 408 382, U.S. Pat. No. 5,310,723 and WO 90/15057).

The aniline derivatives of the formula XV are also known or can be prepared by means of known processes (see in particular EP-A 477 677).

If not stated otherwise, all processes described above are expediently performed at atmospheric pressure or under the autogenous pressure of the respective reaction mixture.

Depending on the substitution pattern of the target compounds, it may be advisable to change the sequence of individual reaction steps in order that certain by-products are not formed or only formed in a small amount.

Working up of the reaction mixtures is carried out as a rule by methods known per se, for example by removing the solvent, partitioning the residue in a mixture of water and a suitable organic solvent and working up the organic phase for the product.

The 3-aryluracils of the formula I can contain one or more chiral centers and are then customarily obtained as enantiomer or diastereomer mixtures if a specific synthesis of one isomer is not performed. The mixtures, if desired, can be separated into the largely pure isomers by the methods customary for this purpose, eg. by means of crystallization or chromatography on an optically active adsorbate. Pure optically active isomers can also be prepared, for example, from corresponding optically active starting materials.

3-Aryluracils I in which A is hydrogen can be converted in a manner known per se into their salts, preferably into their alkali metal salts.

Salts of I whose metal ion is not an alkali metal ion can be prepared by double decomposition of the corresponding alkali metal salt in a customary manner, just as ammonium, phosphonium, sulfonium and sulfoxonium salts can be prepared by means of ammonia, phosphonium, sulfonium or sulfoxonium hydroxides.

The compounds I and their agriculturally utilizable salts are suitable as herbicides, both as isomer mixtures and in the form of the pure isomers. The herbicidal compositions containing I very effectively control plant growth on uncultivated areas, especially at high application rates. They are effective against broad-leafed weeds and grass weeds in crops such as wheat, rice, maize, soybeans and cotton without noticeably damaging the crop plants. This effect occurs especially at low application rates.

Depending on the particular application method, the compounds I or herbicidal compositions containing them can additionally be employed in a further number of crop plants for eliminating undesired plants. Suitable crops, for example, are the following: *Allium cepa, Ananas comosus, Arachis hypogaea, Asparagus officinalis, Beta vulgaris* spp. altissima, *Beta vulgaris* spp. rapa, *Brassica napus* var. napus, *Brassica napus* var. napobrassica, *Brassica rapa* var. silvestris, *Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spp., *Manihot esculenta, Medicago sativa,* Musa spp., *Nicotiana tabacum* (*N. rustica*), *Olea europaea, Oryza sativa, Phaseolus lunatus, Phaseolus vulgaris, Picea abies,* Pinus spp., *Pisum sativum, Prunus avium, Prunus persica, Pyrus communis, Ribes sylvestre, Ricinus communis, Saccharum officinarum, Secale cereale, Solanum tuberosum, Sorghum bicolor* (*S. vulgare*), *Theobroma cacao, Trifolium pratense, Triticum aestivum, Triticum durum, Vicia faba, Vitis vinifera, Zea mays.*

Moreover, the compounds I can also be used in crops which are tolerant to the action of herbicides as a result of breeding, including genetic engineering methods. In addition, the 3-aryluracils I are also suitable for the desiccation and/or defoliation of plants.

As desiccants, they are in particular suitable for the desiccation of the above-ground parts of crop plants such as potato, oilseed rape, sunflower and soybean. Completely mechanized harvesting of these important crop plants is thus made possible.

Of economic interest is also the facilitation of harvesting, which is made possible by the temporally concentrated decrease or reduction in the power of adhesion to the tree in the case of citrus fruits, olives or in the case of other species and varieties of pomes, drupes and indehiscent fruit. The same mechanism, that is the promotion of the formation of separating tissue between fruit or leaf and stem part of the plants is also essential for a highly controllable defoliation of useful plants, in particular cotton.

Additionally, the shortening of the time interval in which the individual cotton plants become ripe leads to an enhanced fiber quality after harvesting.

The compounds I or the compositions containing them can be applied by spraying, atomizing, dusting, broadcasting or watering, for example in the form of directly sprayable aqueous solutions, powders, suspensions, also high-percentage aqueous, oily or other suspensions or dispersions, emulsions, oil dispersions, pastes, dusting compositions, broadcasting compositions or granules. The application forms depend on the intended uses; in each case if possible, they should guarantee the finest dispersion of the active compounds according to the invention.

Suitable inert auxiliaries for the production of directly sprayable solutions, emulsions, pastes or oil dispersions are essentially: mineral oil fractions of medium to high boiling point such as kerosene and diesel oil, also coal tar oils and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, eg. amines such as N-methylpyrrolidone and water.

Aqueous application forms can be prepared from emulsion concentrates, suspensions, pastes, wettable powders or water-dispersible granules by addition of water. For the production of emulsions, pastes or oil dispersions, the substances as such or dissolved in an oil or solvent can be homogenized in water by means of wetting agents, adherents, dispersants or emulsifiers. However, concentrates consisting of active substance, wetting agents, adherents, dispersants or emulsifiers and possibly solvents or oil can also be prepared, which are suitable for dilution with water.

Suitable surface-active substances (adjuvants) are the alkali metal, alkaline earth metal or ammonium salts of aromatic sulfonic acids, eg. lignosulfonic acid, phenolsulfonic acid, naphthalenesulfonic acid and dibutylnaphthalenesulfonic acid, as well as of fatty acids, alkyl- and alkylarylsulfonates, alkyl, lauryl ether and fatty alcohol sulfates, and also salts of sulfated hexa-, hepta- and octadecanols, as well as of fatty alcohol glycol ethers, condensation products of sulfonated naphthalene and its derivatives with formaldehyde, condensation products of naphthalene or of the naphthalenesulfonic acids with phenol and formaldehyde, polyoxyethylene octylphenyl ether, ethoxylated isooctyl-, octyl- or nonylphenol, alkylphenyl and tributylphenyl polyglycol ethers, alkylaryl polyether alcohols, isotridecyl alcohol, fatty alcohol ethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Powder, broadcasting and dusting compositions can be produced by mixing or joint grinding of the active substances with a solid carrier.

Granules, eg. coated, impregnated and homogeneous granules can be produced by binding the active compounds to solid carriers. Solid carriers are mineral earths such as silicic acids, silica gels, silicates, talc, kaolin, limestone, lime, chalk, bole, loess, clay, dolomite, diatomaceous earth, calcium sulfate and magnesium sulfate, magnesium oxide, ground plastics, fertilizers such as ammonium sulfate, ammonium phosphate, ammonium nitrate, ureas and vegetable products such as cereal meal, tree bark, wood and nutshell meal, cellulose powder or other solid carriers.

The concentrations of the active compounds I in the ready-to-apply preparations can be varied within wide ranges. In general, the formulations contain about 0.001 to 98% by weight, preferably 0.01 to 95% by weight, of active compound. The active compounds are in this case employed in a purity of from 90% to 100%, preferably 95% to 100% (according to NMR spectrum).

The following formulation examples illustrate the production of such preparations:

I. 20 parts by weight of the compound No. I.03 are dissolved in a mixture which consists of 80 parts by weight of alkylated benzene, 10 parts by weight of the addition product of from 8 to 10 mol of ethylene oxide to 1 mol of oleic acid N-monoethanolamide, 5 parts by weight of calcium salt of dodecylbenzenesulfonic acid and 5 parts by weight of the addition product of 40 mol of ethylene oxide to 1 mol of castor oil. By pouring the solution out and finely dispersing it in 100,000 parts by weight of water, an aqueous dispersion is obtained which contains 0.02% by weight of the active compound.

II. 20 parts by weight of the compound No. I.04 are dissolved in a mixture which consists of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

III. 20 parts by weight of the active compound No. I.06 are dissolved in a mixture which consists of 25 parts by weight of cyclohexanone, 65 parts by weight of a mineral oil fraction of boiling point 210 to 280° C. and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

IV. 20 parts by weight of the active compound No. I.07, 3 parts by weight of the sodium salt of diisobutylnaphthalene-α-sulfonic acid, 17 parts by weight of the sodium salt of a lignosulfonic acid from a sulfite waste liquor and 60 parts by weight of powdered silica gel are mixed well and ground in a hammer mill. By finely dispersing the mixture in 20,000 parts by weight of water, a spray liquor is obtained which contains 0.1% by weight of the active compound.

V. 3 parts by weight of the active compound No. I.08 are mixed with 97 parts by weight of finely divided kaolin. A dusting composition is obtained in this manner which contains 3% by weight of the active compound.

VI. 20 parts by weight of the active compound No. I.09 are intimately mixed with 2 parts by weight of the calcium salt of dodecylbenzenesulfonic acid, 8 parts by weight of fatty alcohol polyglycol ether, 2 parts by weight of the sodium salt of a phenol-urea-formaldehyde condensate and 68 parts by weight of a paraffinic mineral oil. A stable oily dispersion is obtained.

VII. 1 part by weight of compound No. I.10 is dissolved in a mixture consisting of 70 parts by weight of cyclohexanone, 20 parts by weight of ethoxylated isooctylphenol and 10 parts by weight of ethoxylated castor oil. A stable emulsion concentrate is obtained.

VIII. 1 part by weight of compound No. I.11 is dissolved in a mixture consisting of 80 parts by weight of cyclohexanone and 20 parts by weight of Emulphor EL (ethoxylated castor oil). A stable emulsion concentrate is obtained.

The application of the active compounds I or of the herbicidal compositions can be carried out pre-emergence or post-emergence. If the active compounds are less tolerable to certain crop plants, application techniques can be used in which the herbicidal compositions are sprayed with the aid of the spray equipment such that the leaves of the sensitive crop plants are not affected if possible, while the active compounds reach the leaves of undesired plants growing under them or the uncovered soil surface (post-directed, lay-by).

The application rates of active compound I are, depending on the target to be controlled, time of year, target plants and stage of growth, from 0.001 to 3.0, preferably 0.01 to 1 kg/ha of active substance (a.s.).

For widening the spectrum of action and for achieving synergistic effects, the 3-aryluracils I can be mixed with numerous representatives of other herbicidal or growth-regulating active compound groups and applied together. For example, suitable mixture components are 1,2,4-thiadiazoles, 1,3,4-thiadiazoles, amides, aminophosphoric acid and derivatives thereof, aminotriazoles, anilides, aryloxy/hetaryloxyalkanoic acids and derivatives there-of, benzoic acid and derivatives thereof, benzothiadiazinones, 2-(hetaroyl/aroyl)-1,3-cyclohexanediones, hetaryl aryl ketones, benzylisoxazolidinones, meta-$CF_3$-phenyl derivatives, carbamates, quinolinecarboxylic acid and derivatives thereof, chloroacetanilides, 1,3-cyclohexanedione derivatives, diazines, dichloropropionic acid and derivatives thereof, dihydrobenzofurans, dihydro-3-furanones, dinitroanilines, dinitrophenols, diphenyl ethers, dipyridyls, halo carboxylic acids and derivatives there-of, ureas, 3-phenyluracils, imidazoles, imidazolines, N-phenyl-3,4,5,6-tetrahydrophthalimides, oxadiazoles, oxiranes, phenols, aryloxy- and hetaryloxyphenoxypropionic esters, phenylacetic acid and derivatives thereof, 2-phenylpropionic acid and derivatives thereof, pyrazoles, phenylpyrazoles, pyridazines, pyridinecarboxylic acid and derivatives thereof, pyrimidyl ethers, sulfonamides, sulfonylureas, triazines, triazinones, triazolinones, triazolecarboxamides and uracils.

It may additionally be of use to mix the compounds I, on their own or in combination with other herbicides, additionally with further crop protection compositions and to apply them together, for example with pesticides or compositions against phytopathogenic fungi and against bacteria. Additionally of interest is the miscibility with mineral salt solutions, which are employed for the elimination of nutritional and trace element deficiencies. Non-phytotoxic oils and oil concentrates can also be added.

Preparation Examples

EXAMPLE 1

3-[7-Fluoro-4-hydroxy-4H-2,3-dihydrobenzoxazin-3-on-6-yl]-1-methyl-6-trifluoromethyl-1,2,3,4-tetrahydropyrimidine-2,4-dione (compound 1.01)

A suspension of 3-[4-butoxycarbonylmethoxy-2-fluoro-5-nitrophenyl ]-1-methyl-6-trifluoromethyl-1,2,3,4-tetrahydropyrimidine-2,4-dione (23 g), palladium on carbon (5% strength; 1 g) in 200 ml of N-methylmorpholine was hydrogenated at from 25 to 20° C. using a hydrogen overpressure of 0.1 bar. After adsorption of 2.14 l of hydrogen, the solvent was removed at from 50 to 55° C. in an oil pump vacuum. The residue was taken up using 200 ml of dichloromethane, after which the solution was washed three times with water and then dried over sodium sulfate. Yield: 20 g.

EXAMPLE 2

3-[7-Fluoro-4-propargyloxy-4H-2,3-dihydrobenzoxazin-3-on-6-yl]-1-methyl-6-trifluoromethyl-1,2,3,4-tetrahydropyrimidine-2,4-dione (compound 1.05)

Potassium carbonate (0.76 g) and 3-bromopropyne (0.41 ml) were added to a solution of 3-[7-fluoro-4-hydroxy-4H-2,3-dihydrobenzoxazin-3-on-6-yl]-1-methyl-6-trifluoromethyl-1,2,3,4-tetrahydropyrimidine-2,4-dione (1.9 g) in 100 ml of N,N-dimethylformamide.

After stirring at about 20° C. for 5 hours, the solvent was removed, and the residue was taken up in 150 ml of dichloromethane and washed three times with 30 ml of water each time. The organic phase was dried over sodium sulfate and then freed from the solvent. After chromatography on silica gel (eluent: dichloromethane/ethyl acetate 9:1), 0.5 g of valuable product was obtained.

EXAMPLE 3

3-[4-Amino-7-fluoro-4H-2,3-dihydrobenzoxazin-3-on-6-yl]-1-methyl-6-trifluoromethyl-1,2,3,4-tetrahydropyrimidine-2,4-dione (compound 1.03)

Potassium carbonate (2.8 g) and 2,4-dinitrophenoxyamine (2.2 g) were added to a solution of 3-[7-fluoro-4H-2,3-dihydrobenzoxazin-3-on-6-yl]-1-methyl-6-trifluoromethyl-1,2,3,4-tetrahydropyrimidine-2,4-dione (3.6 g) in 50 ml of ethyl acetate. The reaction mixture was then stirred for 10 hours at from 45 to 50° C. After cooling, the resulting solid fraction was separated off and valuable product contained therein washed out with diisopropyl ether. The diisopropyl ether phase was then combined with the solid-free reaction solution. The organic phase thus obtained was washed twice with 25 ml of water each time, dried over sodium sulfate and then concentrated.

As according to $^1$H-NMR spectrum the whole amount of starting compound had not reacted, the mixture was reaminated again using potassium carbonate (1.1 g) and 2,4-dinitrophenoxyamine (0.8 g). Working up was carried out as described above. Total yield: 1.2 g.

EXAMPLE 4

3-[4-Acetoxy-7-fluoro-4H-2,3-dihydrobenzoxazin-3-on-6-yl]-1-methyl-6-trifluoromethyl-1,2,3,4-tetrahydropyrimidine-2,4-dione (Cpd. 1.07)

Potassium carbonate (0.76 g) and acetyl chloride (0.39 ml) were added to a solution of 3-[7-fluoro-4-hydroxy-4H-2,3-dihydrobenzoxazin-3-on-6-yl]-1-methyl-6-trifluoromethyl-1,2,3,4-tetrahydropyrimidine-2,4-dione (1.9 g) in 100 ml of N,N-dimethylformamide. After stirring at room temperature for 5 hours, the solvent was removed. The residue was taken up in 150 ml of dichloromethane. The organic phase was washed three times with 30 ml of water each time, subsequently dried over sodium sulfate and then concentrated. After chromatography on silica gel (eluent: dichloromethane/ethyl acetate 9:1), 0.5 g of valuable product was obtained.

In addition to the compounds described above, still further 3-aryluracils I which were prepared or can be prepared in an analogous manner are listed in the following Table 2:

TABLE 2

$I(Y^1, Y^2 = O; R^5, R^6 = H)$

| No. | A | $R^1$ | $R^2$ | $R^3$ | Z | X | $R^4$ | M.p.[° C.] |
|---|---|---|---|---|---|---|---|---|
| 1.01 | $CH_3$ | F | $CF_3$ | H | —O— | —O— | H | 118–120 |
| 1.02 | $CH_3$ | F | $CF_3$ | H | —O— | —O— | $CH_3$ | 154–156 |
| 1.03 | $CH_3$ | F | $CF_3$ | H | —O— | —NH— | H | 220–222 |
| 1.04 | $CH_3$ | F | $CF_3$ | H | —O— | —O— | $CH_2CH\!=\!CH_2$ | 132–134 |
| 1.05 | $CH_3$ | F | $CF_3$ | H | —O— | —O— | $CH_2C\!\equiv\!CH$ | 125–127 |
| 1.06 | $CH_3$ | F | $CF_3$ | H | —O— | —O— | $CH_2COOCH_3$ | 139–140 |
| 1.07 | $CH_3$ | F | $CF_3$ | H | —O— | —O— | $COCH_3$ | 157–159 |
| 1.08 | $CH_3$ | F | $CF_3$ | H | —O— | —O— | $CH_2CH_3$ | 110–112 |
| 1.09 | $CH_3$ | F | $CF_3$ | H | —NH— | —NH— | H | 208 (decomp.) |
| 1.10 | $CH_3$ | F | $CF_3$ | H | —O— | —N($COCH_3$)— | $COCH_3$ | 220–222 |
| 1.11 | $NH_2$ | F | $CF_3$ | H | —O— | —O— | $CH_2CH_3$ | 181–183 |
| 1.12 | $NH_2$ | F | $CF_3$ | H | —O— | —O— | $CH_3$ | 194–195 |
| 1.13 | $NH_2$ | F | $CF_3$ | H | —O— | —O— | $CH_2CH\!=\!CH_2$ | 128–130 |
| 1.14 | $NH_2$ | F | $CF_3$ | H | —O— | —O— | H | 120–135 |
| 1.15 | $NH_2$ | F | $CF_3$ | H | —O— | —O— | $(CH_2)_2CH_2F$ | 115–117 |
| 1.16 | $NH_2$ | F | $CF_3$ | H | —O— | —O— | $(CH_2)_2OCH_3$ | 99–103 |
| 1.17 | $NH_2$ | F | $CF_3$ | H | —O— | —O— | $n\text{-}C_4H_9$ | 130–138 |
| 1.18 | $NH_2$ | F | $CF_3$ | H | —O— | —O— | $CH_2CN$ | 208–210 |
| 1.19 | $NH_2$ | F | $CF_3$ | H | —O— | —O— | $CH_2$ phenyl | 180–182 |
| 1.20 | $NH_2$ | F | $CF_3$ | H | —O— | —O— | (CO—$CH_3$) | 139–140 |
| 1.21 | $NH_2$ | F | $CF_3$ | H | —O— | —O— | $(CHCH_3)_2$ | 155–157 |
| 1.22 | $NH_2$ | F | $CF_3$ | H | —O— | —O— | cyclohex-2-enyl | 125–128 |
| 1.23 | $NH_2$ | F | $CF_3$ | H | —O— | —O— | $CH(CH_3)$—CO—$CH_3$ | 128–130 |

Use examples (herbicidal activity)

It was possible to show the herbicidal action of the 3-aryluracils I by the following greenhouse tests:

The cultivation containers used were plastic flowerpots containing loamy sand with about 3.0% humus as a substrate. The seeds of the test plants were sown separately according to species.

In the case of pre-emergence treatment, the active compounds suspended or emulsified in water were applied directly after sowing by means of finely dispersing nozzles. The containers were lightly watered to promote germination and growth, and then covered with transparent plastic hoods until the plants had taken root. This covering causes uniform germination of the test plants if this has not been adversely affected by the active compounds.

For the purpose of post-emergence treatment, the test plants were first raised, depending on growth form, up to a growth height of from 3 to 15 cm, and only then treated with the active compounds suspended or emulsified in water. For this purpose, the test plants were either sown directly and cultivated in the same containers or they were first raised separately as seedlings and transplanted into the test containers a few days before treatment. The application rate for post-emergence treatment was 0.0078 or 0.0039 kg/ha of a.s. (active substance).

The plants were kept in a species-specific manner at 10–25° C. or 20–35° C. The test period extended over 2 to 4 weeks. During this time, the plants were tended and their reaction to the individual treatments was evaluated.

Assessment was carried out on a scale from 0 to 100. 100 in this case means no emergence of the plants or complete destruction at least of the above-ground parts and 0 means no damage or normal course of growth.

The plants used in the greenhouse tests consisted of the following species:

| Botanical name | Common name |
|---|---|
| *Abutilon theophrasti* | velvet leaf |
| Ipomoea subspecies | morning-glory |
| *Solanum nigrum* | black nightshade |
| Veronica subspecies | speedwell |

At an application rate of 0.0078 or 0.0039 kg/ha of a.s. the compound No. I.08 showed a very good action against the abovementioned plants postemergence.

Use Examples (Desiccant/Defoliant Activity)

The test plants used were young, 4-leafed (without seed leaves) cotton plants, which were raised under greenhouse conditions (rel. atmospheric humidity 50 to 70%; day/night temperature=27/20° C.).

The young cotton plants were subjected to foliar treatment until dripping wet with aqueous preparations of the active compounds (with addition of 0.15% by weight of the fatty alcohol alkoxylate Plurafac LF 700, based on the spray liquor). The amount of water applied was the equivalent of 1000 l/ha. After 13 days, the number of leaves shed and the degree of defoliation was determined in %.

In the case of the untreated control plants, no leaf fall occurred.

We claim:

1. A 3-aryluracil of formula I

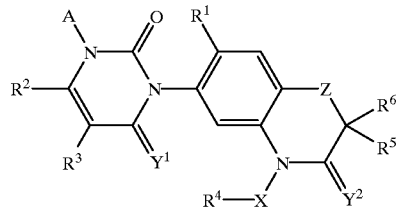

(I)

where the variables have the following meanings:
A is methyl or amino;
$R^1$ is hydrogen or halogen;
$R^2$ is $C_1$–$C_6$-haloalkyl;
$R^3$ is hydrogen;
X is oxygen;
$Y^1$ and $Y^2$ are oxygen;
Z is oxygen;
$R^5$ and $R^6$ independently of one another are hydrogen or $C_1$–$C_6$-alkyl;
$R^4$ is $C_1$–$C_6$-alkyl, $C_3$–$C_6$-alkenyl or $C_3$–$C_6$-alkynyl.

2. The 3-aryluracil of formula I defined in claim 1, wherein
A is methyl; and
$R^1$ is hydrogen, fluorine or chlorine.

3. The 3-eryluracil of formula I defined in claim 1, wherein $R^2$ is trifluoromethyl, chlorodifluoromethyl or pentafluoroethyl.

4. An enamino ester of formula IV

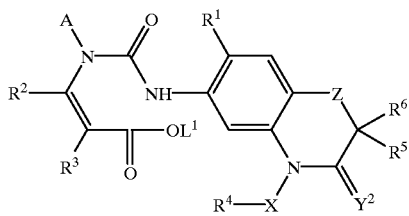

(IV)

where
$L^1$ is $C_1$–$C_6$-alkyl or phenyl,
A is methyl or amino;
$R^1$ is hydrogen or halogen;
$R^2$ is $C_1$–$C_6$-haloalkyl;
$R^3$ is hydrogen;
X is oxygen;
$Y^1$ and $Y^2$ are oxygen;
Z is oxygen;
$R^5$ and $R^6$ independently of one another are hydrogen or $C_1$–$C_6$-alkyl;
$R^4$ is $C_1$–$C_6$-alkyl, $C_3$–$C_6$-alkenyl or $C_3$–$C_6$-alkynyl.

5. An enamino carboxylate of formula V

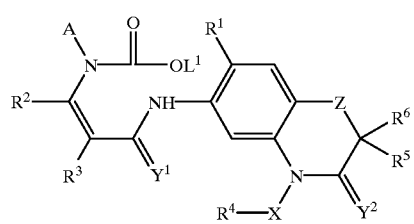

(V)

where
$L^1$ is $C_1$–$C_6$-alkyl or phenyl,
A is methyl or amino;
$R^1$ is hydrogen or halogen;
$R^2$ is $C_1$–$C_6$-haloalkyl;
$R^3$ is hydrogen;
X is oxygen;
$Y^1$ and $Y^2$ are oxygen;
Z is oxygen;
$R^5$ and $R^6$ independently of one another are hydrogen or $C_1$–$C_6$-alkyl;
$R^4$ is $C_1$–$C_6$-alkyl, $C_3$–$C_6$-alkenyl or $C_3$–$C_6$-alkynyl.

6. A herbicidal composition comprising a herbicidally active amount of a 3-aryluracil of formula I or an agriculturally utilizable salt of I, as defined in claim 1, and at least one inert liquid or solid carrier and optionally at least one surfactant.

7. A composition for the desiccation or defoliation of plants, comprising an amount of a 3-aryluracil of formula I or an agriculturally utilizable salt of I, having desiccant or defoliant activity, as defined in claim 1, and at least one inert liquid or solid carrier and optionally at least one surfactant.

8. A method of controlling undesired vegetation, which comprises allowing a herbicidally active amount of a 3-aryluracil of formula I or an agriculturally utilizable salt of I, as defined in claim 1, to act on plants, their habitat or on seeds.

9. A method for the desiccation or defoliation of plants, which comprises allowing an amount of a 3-aryluracil of formula I or an agriculturally utilizable salt of I, having desiccant or defoliant activity, as defined in claim 1, to act on plants.

* * * * *